US011419510B2

(12) United States Patent
Matsuura

(10) Patent No.: US 11,419,510 B2
(45) Date of Patent: Aug. 23, 2022

(54) BIOLOGICAL SENSOR MODULE AND BIOLOGICAL INFORMATION MEASURING APPARATUS

(71) Applicant: SEIKO EPSON CORPORATION, Tokyo (JP)

(72) Inventor: Katsutoshi Matsuura, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 411 days.

(21) Appl. No.: 16/516,320

(22) Filed: Jul. 19, 2019

(65) Prior Publication Data

US 2020/0022598 A1    Jan. 23, 2020

(30) Foreign Application Priority Data

Jul. 20, 2018  (JP) .............................. JP2018-136351

(51) Int. Cl.
*A61B 5/024* (2006.01)
*A61B 5/00* (2006.01)

(52) U.S. Cl.
CPC ........ *A61B 5/02416* (2013.01); *A61B 5/0059* (2013.01); *A61B 5/681* (2013.01); *A61B 5/6843* (2013.01)

(58) Field of Classification Search
None
See application file for complete search history.

(56) References Cited

U.S. PATENT DOCUMENTS

| 2011/0190605 A1* | 8/2011 | Yamashita | A61B 5/02438 600/310 |
| 2016/0192879 A1* | 7/2016 | Yamashita | A61B 5/721 600/407 |
| 2017/0086743 A1* | 3/2017 | Bushnell | A61B 5/681 |
| 2017/0112398 A1* | 4/2017 | Narusawa | A61B 5/681 |

FOREIGN PATENT DOCUMENTS

JP    2017-000314 A    1/2017

* cited by examiner

*Primary Examiner* — Shahdeep Mohammed
(74) *Attorney, Agent, or Firm* — Oliff PLC

(57) ABSTRACT

A biological sensor module includes a light emitter that emits irradiation light with which a living body is irradiated, a light receiver that receives reflected light that is the irradiation light reflected off the living body, and a passage section through which the irradiation light and the reflected light pass. The passage section includes an outer surface section that comes into contact with the living body and an inner surface section that is opposite the outer surface section. The outer surface section has a first convex curved surface that presses the living body, and the inner surface section has a second convex curved surface that collects the reflected light incident on the passage section into a spot on the light receiver.

13 Claims, 15 Drawing Sheets

BIOLOGICAL SENSOR MODULE AND BIOLOGICAL INFORMATION MEASURING APPARATUS

The present application is based on, and claims priority from JP Application Serial Number 2018-136351, filed Jul. 20, 2018, the disclosure of which is hereby incorporated by reference herein in its entirety.

BACKGROUND

1. Technical Field

The present disclosure relates to a biological sensor module and a biological information measuring apparatus.

2. Related Art

There has been a known pulse wave meter that measures the pulse wave as a biological information measuring apparatus that measures biological information (see JP-A-2017-314, for example).

The pulse wave meter described in JP-A-2017-314 includes a pulse wave sensor, a filter, an amplifier, an A/D circuit, and a controller. The pulse wave sensor includes an LED (light emitting diode), a PD (photodiode), and a lens. The LED emits light in the forward direction through the lens, and the PD receives reflected light incident through the lens. The filter removes noise from a detection signal from the PD, and the amplifier amplifies the detection signal from which noise has been removed. The A/D circuit converts the amplified detection signal into a digital signal, and the controller measures the pulse wave of the subject based on the detection signal.

JP-A-2017-314 is an example of the related art.

A change in the volume of a blood vessel increases when the difference between the pressure in a blood vessel and the pressure outside the blood vessel is close to 0. In other words, applying pressure close to the blood pressure to a blood vessel allows a large increase in a change in the volume of the blood vessel. In this case, since a signal based on the amount of light reflected off the blood vessel and received with a light receiver changes greatly, the frequency of the pulse is readily extracted, and the pulse rate is therefore readily calculated. Therefore, it is believed in the pulse wave meter described in JP-A-2017-314 described above that a curved surface of the lens that is the curved surface in contact with the subject's finger presses the subject's finger to apply predetermined pressure thereto.

In the pulse wave meter described in JP-A-2017-314, however, the lens through which the light reflected off the subject's finger passes is not so optimized as to collect the incident light into a spot on the PD while applying the predetermined pressure to the subject's finger. Therefore, even if the light originating from the LED is collected into a spot on the PD, an unstable state of the contact between the subject's finger and the lens could mix a large amount of outside light (noise light) with the light originating from the LED. In this case, the S/N ratio of the pulse signal cannot undesirably be sufficiently increased.

SUMMARY

A biological sensor module according to a first aspect of the present disclosure includes a light emitter that emits irradiation light with which a living body is irradiated, a light receiver that receives reflected light that is the irradiation light reflected off the living body, and a passage section through which the irradiation light and the reflected light pass. The passage section includes an outer surface section that comes into contact with the living body and an inner surface section that is opposite the outer surface section. The outer surface section has a first convex curved surface that presses the living body, and the inner surface section has a second convex curved surface that collects the reflected light incident on the passage section into a spot on the light receiver. A radius of curvature of the second convex curved surface is smaller than a radius of curvature of the first convex curved surface in a cross section parallel to a plane specified by a first direction that is a direction from the light emitter toward the light receiver and a second direction that is a direction from the inner surface section toward the outer surface section.

In the first aspect described above, a center of the second convex curved surface may be so set as to fall within a range including a center of the light receiver and a center of the first convex curved surface and between the center of the light receiver and the center of the first convex curved surface when viewed along the second direction.

In the first aspect described above, the second convex curved surface may have a portion that does not overlap with the light receiver when viewed along the second direction.

In the first aspect described above, the inner surface section may include a recess that is recessed in the second direction, and that the second convex curved surface is located in the recess.

In the first aspect described above, the inner surface section may be located in the recess and has a concave curved surface continuous with an outer edge of the second convex curved surface.

A biological information measuring apparatus according to a second aspect of the present disclosure includes the biological sensor module described above, a housing in which the biological sensor module is provided, and a processing section that calculates biological information based on a signal outputted from the light receiver.

In the second aspect described above, the housing may include a contact section that has an opening in which the passage section is disposed and comes into contact with the living body, and a center of the first convex curved surface may substantially coincide with a center of the contact section when viewed along the second direction.

DESCRIPTION OF EXEMPLARY EMBODIMENTS

First Embodiment

A first embodiment of the present disclosure will be described below with reference to the drawings.
Schematic Configuration of Biological Information Measuring Apparatus FIG. 1 is a front view showing a biological information measuring apparatus 1A according to the present embodiment.

The biological information measuring apparatus 1A according to the present embodiment is a wearable instrument that is worn, when used, on the body of a user who is a living body and measures biological information associated with the user. Specifically, the biological information measuring apparatus 1A is an instrument that is worn on the user's wrist or any other apparatus worn portion, detects the pulse wave, which is the biological information, and measures the pulse rate, which is also the biological information.

Figure 1:
FIG. 1 is a front view showing a biological information measuring apparatus according to a first embodiment of the present disclosure.
Figure 1:
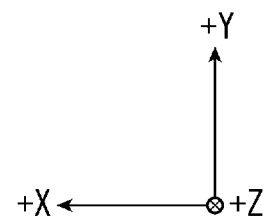

The biological information measuring apparatus 1A includes a housing 2 and bands BN1 and BN2, which are attached to the housing 2, as shown in FIG. 1. The housing 2 includes a front surface section 21, which includes a display window that allows the user who wears the biological information measuring apparatus 1A to visually recognize the biological information displayed in a display section 51, and a rear surface section 22, which comes into contact with the subject's body when the user wears the biological information measuring apparatus 1A.
Configuration of Bands The band BN1 extends from one end of the housing 2, and the band BN2 extends from the other end of the housing 2 when the bands BN1 and BN2 are viewed from a position facing the front surface section 21 of the housing 2. That is, the bands BN1 and BN2 extend from the opposite ends of the housing 2 in the direction in which the bands BN1 and BN2 separate away from each other. The housing 2 is worn on the wearing portion when the bands BN1 and BN2 are linked to each other via a buckle (not shown). The bands BN1 and BN2 may instead be formed integrally with the housing 2.

In the following description, the direction from the front surface section 21 toward the rear surface section 22 is called a direction +Z. The directions perpendicular to the direction +Z and perpendicular to each other are called a direction +X and a direction +Y. Although not shown, a direction −Z, a direction −X, and a direction −Y are the directions opposite the direction +Z, the direction +X, and the direction +Y, respectively.

In the present embodiment, it is assumed that the direction in which the band BN1 extends is the direction +Y when viewed from the negative side in the direction Z. It is further assumed that the direction +X is the direction from right toward left when the biological information measuring apparatus 1A is so viewed from the negative side in the direction Z that the direction +Y is oriented upward.

Out of the directions defined above, the direction +Z is not only the direction in which a light emitter 83, which will be described later, primarily emits first light, which is illumination light, but the direction along a normal to a light receiving surface 841 of a light receiver 84, which will be described later.

In the following description, a view of a target from the positive side in the direction Z is called a "plan view."
Configuration of Housing The housing 2 includes the front surface section 21 and the rear surface section 22 (see FIG. 3) as described above and further includes a side surface section 23.

The front surface section 21 is provided with the display section 51 described above, and a display window 211 is closed by a light transmissive cover 212.

The side surface section 23 is an annular section formed along the circumferential direction around the direction +Z and connects the front surface section 21 and the rear surface section 22 to each other. Buttons 31 and 32, which form an operation section 3, are disposed in an −X-direction-side area of the side surface section 23, and buttons 33 and 34, which also form the operation section 3, are disposed in an +X-direction-side area of the side surface section 23.

The configuration of the rear surface section 22 will be described later in detail.
Internal Configuration of Biological Information Measuring Apparatus FIG. 2 is a block diagram showing the configuration of the biological information measuring apparatus 1A.

Figure 2:
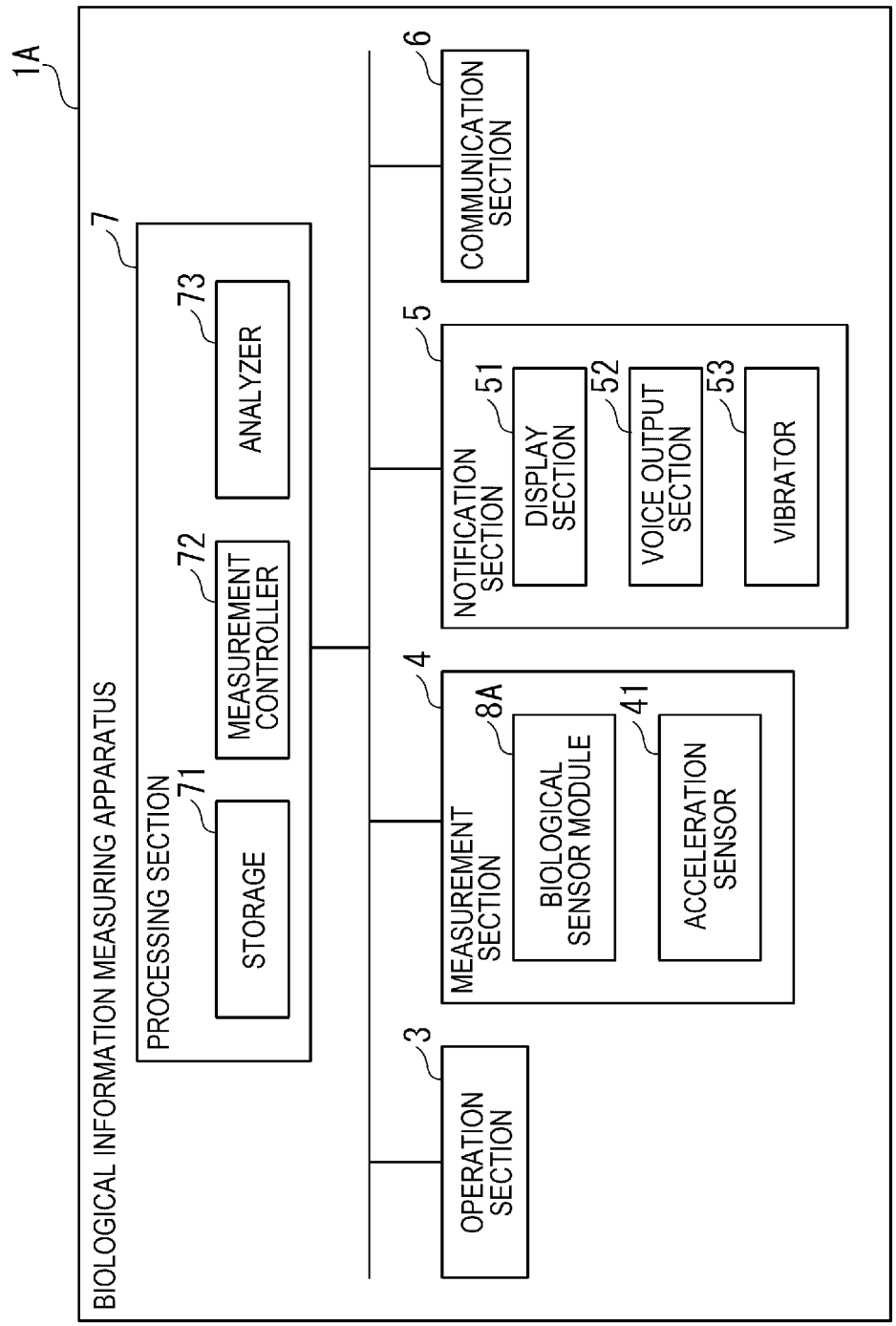
FIG. 2 is a block diagram showing the configuration of the biological information measuring apparatus according to the first embodiment.

The biological information measuring apparatus 1A includes the operation section 3, a measurement section 4, a notification section 5, a communication section 6, and a processing section 7, which are provided in the housing 2, as shown in FIG. 2.

The operation section 3 includes the buttons 31 to 34 described above and outputs an operation signal according to an input performed on any of the buttons 31 to 34 to the processing section 7.

The measurement section 4 outputs results of detection of a variety of pieces of information to the processing section 7. The measurement section 4 includes a biological sensor module 8A, which detects the pulse wave, which is the biological information, and an acceleration sensor 41, which detects acceleration acting on the biological information measuring apparatus 1A. The configuration of the biological sensor module 8A will be described later in detail.

The notification section 5 notifies the user of a variety of pieces of information under the control of the processing section 7. The notification section 5 includes the display section 51, a voice output section 52, and a vibrator 53.

The display section 51 includes a liquid crystal display panel, an electronic paper display panel, or any of a variety of other display panels and displays information inputted from the processing section 7, for example, the pulse rate, which is the biological information associated with the user.

The voice output section 52 outputs voice according to a voice signal inputted from the processing section 7.

The vibrator 53 includes a motor that operates under the control of the processing section 7 and notifies the user, for example, of a warning in the form of vibration produced by the driven motor.

The communication section 6 is a communication module that transmits detected and analyzed biological information to an external instrument and outputs information received from the external instrument to the processing section 7. The communication section 6 wirelessly communicates with the external instrument by using a short-range wireless communication scheme in the present embodiment and may instead communicate with the external instrument via a relay device, such as a cradle, or a cable. Still instead, the communication section 6 may communicate with the external instrument over a network.

The processing section 7 is formed of a circuit substrate including a computation processing circuit and a flash memory and is electrically connected to the operation section 3, the measurement section 4, the notification section 5, and the communication section 6. The processing section 7 controls the action of the entire biological information measuring apparatus 1A autonomously or in accordance with the operation signal inputted from the operation section 3. In addition to the above, the processing section 7 controls the action of the biological sensor module 8A and analyzes a detection signal inputted from the biological sensor module 8A.

The processing section 7 includes a storage 71, which is formed of the flash memory described above, and a measurement controller 72 and an analyzer 73, which are formed of the computation processing circuit described above that executes a program stored in the storage 71.

The storage 71 stores a variety of programs and data necessary for the action of the biological information measuring apparatus 1A. The storage 71 further stores the detection signal inputted from the measurement section 4 and the result of the analysis performed by the analyzer 73.

The measurement controller 72 controls the action of the biological sensor module 8A.

The analyzer 73 analyzes the detection signal inputted from the measurement section 4 to calculate, for example, the pulse rate. The analyzer 73 can calculate the pulse rate by employing a known approach.

Configuration of Rear Surface Section of Housing

Figure 3:
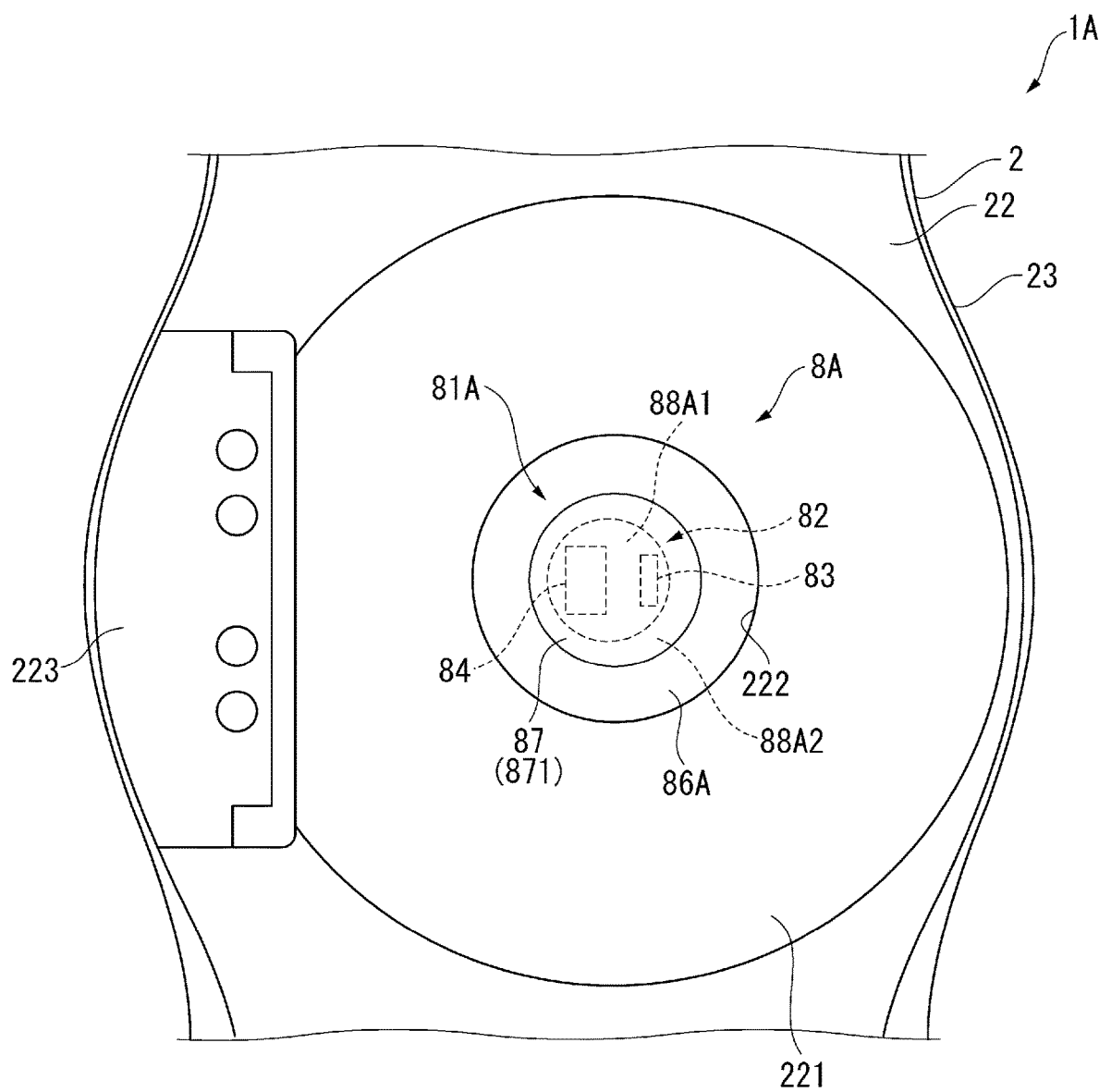
FIG. 3 is a plan view showing a rear surface section of a housing in the first embodiment.

FIG. 3 is a plan view showing the rear surface section 22 of the housing 2. In FIG. 3, the buttons 31 to 34 are omitted.

The rear surface section 22 includes a substantially circular contact section 221, which is located in a central portion of the rear surface section 22 in the plan view and protrudes toward the positive side in the direction Z with the amount of protrusion increasing with distance toward the center of the rear surface section 22. The contact section 221 is a portion that comes into contact with the user's body when the biological information measuring apparatus 1A is worn on the user's body. A circular opening 222 is formed at the center of the contact section 221.

The light emitter 83, the light receiver 84, and a light blocker 85 (not shown in FIG. 3) of the biological sensor module 8A, which will be described later, are disposed in the opening 222, and a passage section 86A, which also forms the biological sensor module 8A, is fit into the opening 222.

A connection section 223, which is connected to a cradle that is not shown, is provided in a −X-direction-side portion of the rear surface section 22.

Configuration of Biological Sensor Module

Figure 4:
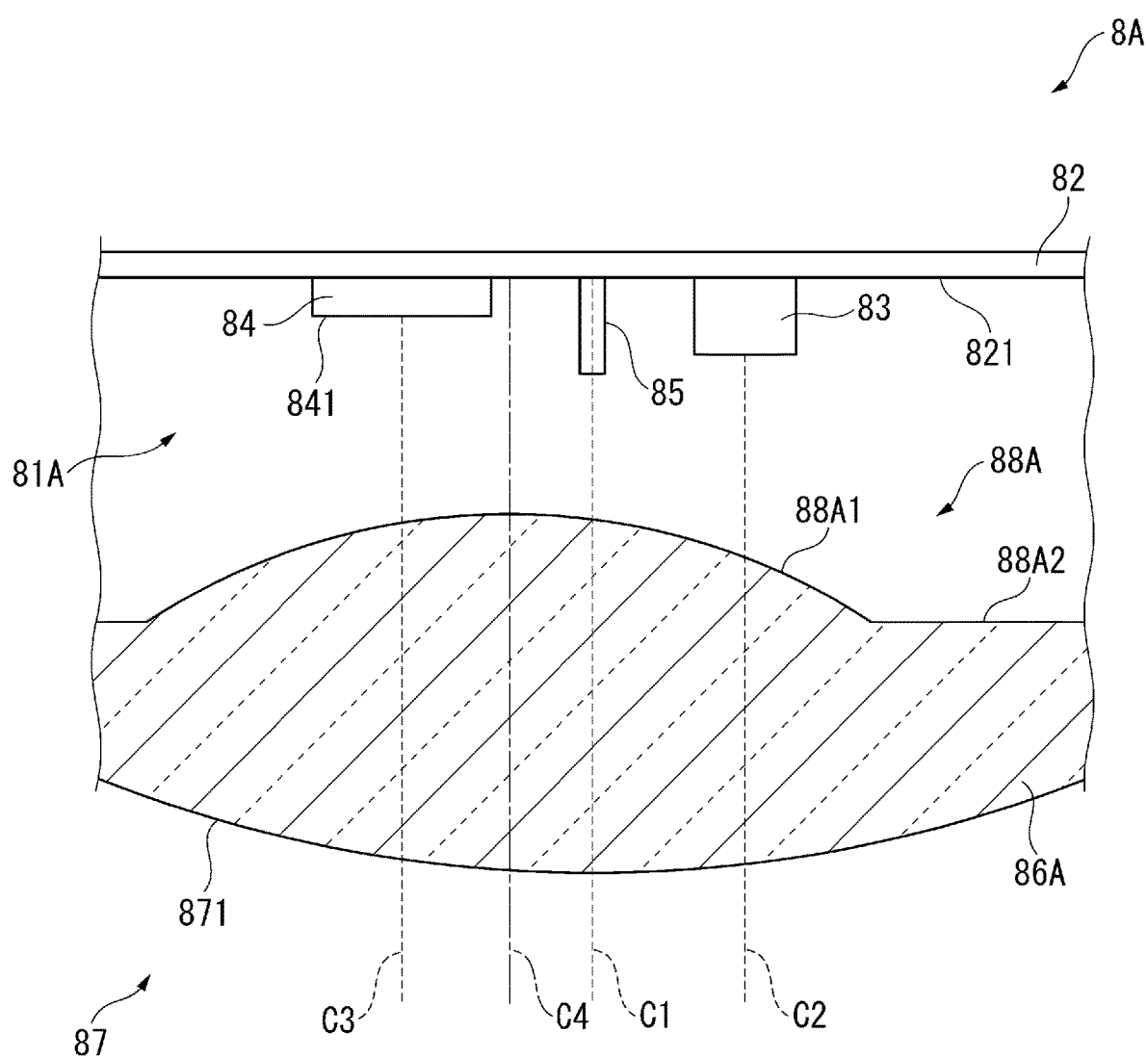
FIG. 4 is a cross-sectional view showing a biological sensor module in the first embodiment.

FIG. 4 shows the cross section of the biological sensor module 8A taken along a plane XZ.

The biological sensor module 8A detects the pulse wave, which is one piece of biological information, and outputs a detection signal representing the pulse wave to the processing section 7. The biological sensor module 8A includes a sensor section 81A and the passage section 86A, which is disposed on the +Z-direction side of the sensor section 81A, as shown in FIGS. 3 and 4.

Configuration of Sensor Section

The sensor section 81A includes a substrate 82 and the light emitter 83, the light receiver 84, and the light blocker 85, which are provided on the substrate 82, as shown in FIG. 4.

The substrate 82 is provided in the housing 2 and supports the light emitter 83, the light receiver 84, and the light blocker 85 on a +Z-direction-side surface 821 of the substrate 82. The substrate 82 supplies the light emitter 83 with electric power and outputs the detection signal outputted from the light receiver 84 to the processing section 7 via a connector that is not shown. The substrate 82 may be a rigid substrate or an FPC (flexible printed circuits).

The light emitter 83 emits first light that is illumination light with which the user's body, which is a living body, is irradiated. Although not illustrated in detail, the light emitter 83 is an LED chip in which a light emitting device, such as a LED (light emitting diode), is encapsulated with a sealing resin. The light emitter 83 may instead be a bare chip in which a light emitting device is not encapsulated with a sealing resin. The first light is green light in the present embodiment and may instead be light having a different wavelength.

The light receiver 84 receives second light incident from the user's body, that is, second light that is the first light that is the illumination light emitted from the light emitter 83 and reflected off the user's body and outputs a detection signal representing the amount of received second light. The light receiver 84 is, although not illustrated in detail, a PD chip in which a light receiving device that is a PD (photodiode) is encapsulated with a sealing resin. The light receiver 84 may instead be a bare chip in which a light receiving device is not encapsulated with a resin.

The light receiving device has, for example, a silicon-substrate-side n-type semiconductor area and a light-receiving-surface-side p-type semiconductor area and outputs current based on the photovoltaic effect when light having sufficiently large energy is incident on the p-type semiconductor area. The light receiving surface 841 of the light receiver 84 is a portion where the p-type semiconductor area is located when viewed from the light incident side of the light receiver 84.

The thus configured light receiver 84 is provided with a wavelength limiting filter that transmits light having substantially the same wavelength as that of the first light but limits the wavelength of the light incident on the light receiving surface 841.

In the present embodiment, the shape of the light receiver 84 in the plan view is formed in a substantially oblong shape that is long in the direction +Y and short in the direction +X, as shown in FIG. 3. The light receiver 84 in the plan view may, however, have a substantially square shape or a substantially oblong shape that is long in the direction +X and short in the direction in +Y.

The light blocker 85 is disposed between the light emitter 83 and the light receiver 84, as shown in FIG. 4, and blocks the light from the light emitter 83 directly toward the light receiver 84 to prevent the first light emitted from the light emitter 83 from being directly incident on the light receiver 84 via no living body.

Configuration of Passage Section

The passage section 86A (light transmissive section) is a light transmissive member that closes the opening 222 to protect the sensor section 81A and transmits the first light emitted from the light emitter 83 and the second light incident from the user's body.

The passage section 86A includes an outer surface section 87, which is a +Z-direction-side portion and comes, along with the contact section 221 into contact with the user's body, and an inner surface section 88A, which is a −Z-direction-side portion opposite the outer surface section 87 and faces the light emitter 83, the light receiver 84, and the light blocker 85.

The outer surface section 87 of the passage section 86A has a first convex curved surface 871, which protrudes toward the positive side in the direction Z and presses the user's body.

The first convex curved surface 871 is a convex curved surface that protrudes toward the positive side in the direction Z with the amount of protrusion increasing with distance toward the center of the convex curved surface in the plan view. The amount of protrusion of the first convex curved surface 871 is so designed as to be large enough to be capable of applying extra-blood-vessel pressure substantially equal to the intra-blood-vessel pressure to the portion irradiated with the first light when the user wears the biological information measuring apparatus 1A.

In the plan view, a center C1 of the first convex curved surface 871 is, although not shown, set substantially at the center of the rear surface section 22, in detail, substantially at the center of the contact section 221. Further, in the plan view, the center C1 is set in a position between a center C2 of the light emitter 83 and a center C3 of the light receiver 84.

The range over which the first convex curved surface 871 is formed is a range where the first convex curved surface 871 covers the entirety of the light emitter 83 and the light receiver 84 in the plan view.

The center C2 of the light emitter 83 represents the position of the center of the light emitting device of the light emitter 83 in the plan view. The center C3 of the light receiver represents the position of the center of the p-type semiconductor area described above, which is the light receiving surface 841 of the light receiver 84 in the plan view. The same holds true in the following description.

The inner surface section 88A has a second convex curved surface 88A1 and a flat surface 88A2. That is, the passage section 86A is formed in a biconvex shape having the first convex curved surface 871, which protrudes toward the positive side in the direction Z, and the second convex curved surface 88A1, which protrudes toward the negative side in the direction Z.

The flat surface 88A2 is formed in an area of the inner surface section 88A that is the area other than the second convex curved surface 88A1.

The second convex curved surface 88A1 has a convexly curved shape having a radius of curvature smaller than that of the first convex curved surface 871 in a cross section parallel to the plane XZ. The plane XZ is a plane specified by an axis X parallel to the direction −X, which is a first direction from the light emitter 83 toward the light receiver 84, and an axis Z parallel to the direction +Z, which is a second direction from the inner surface section 88A toward the outer surface section 87, in the present embodiment.

A center C4 of the second convex curved surface 88A1 in the plan view is so set as to fall within the range including the center C1 of the first convex curved surface 871 and the center C3 of the light receiver 84 and between the center C1 and the center C3.

The range over which the second convex curved surface 88A1 is formed is so set that the second convex curved surface 88A1 has a portion that overlaps with at least part of the light receiver 84 and a portion that does not overlap with the light receiver 84 in the plan view. In the present embodiment, the range over which the second convex curved surface 88A1 is formed is so set that the second convex curved surface 88A1 covers the entire light receiver 84 in the plan view.

The thus formed second convex curved surface 88A1 collects, out of the second light incident on the passage section 86A, not only the second light incident on the area that overlaps with the light receiver 84 but the second light incident on the area that does not overlap with the light receiver 84 in the plan view into a spot on the light receiver 84.

Figure 5:
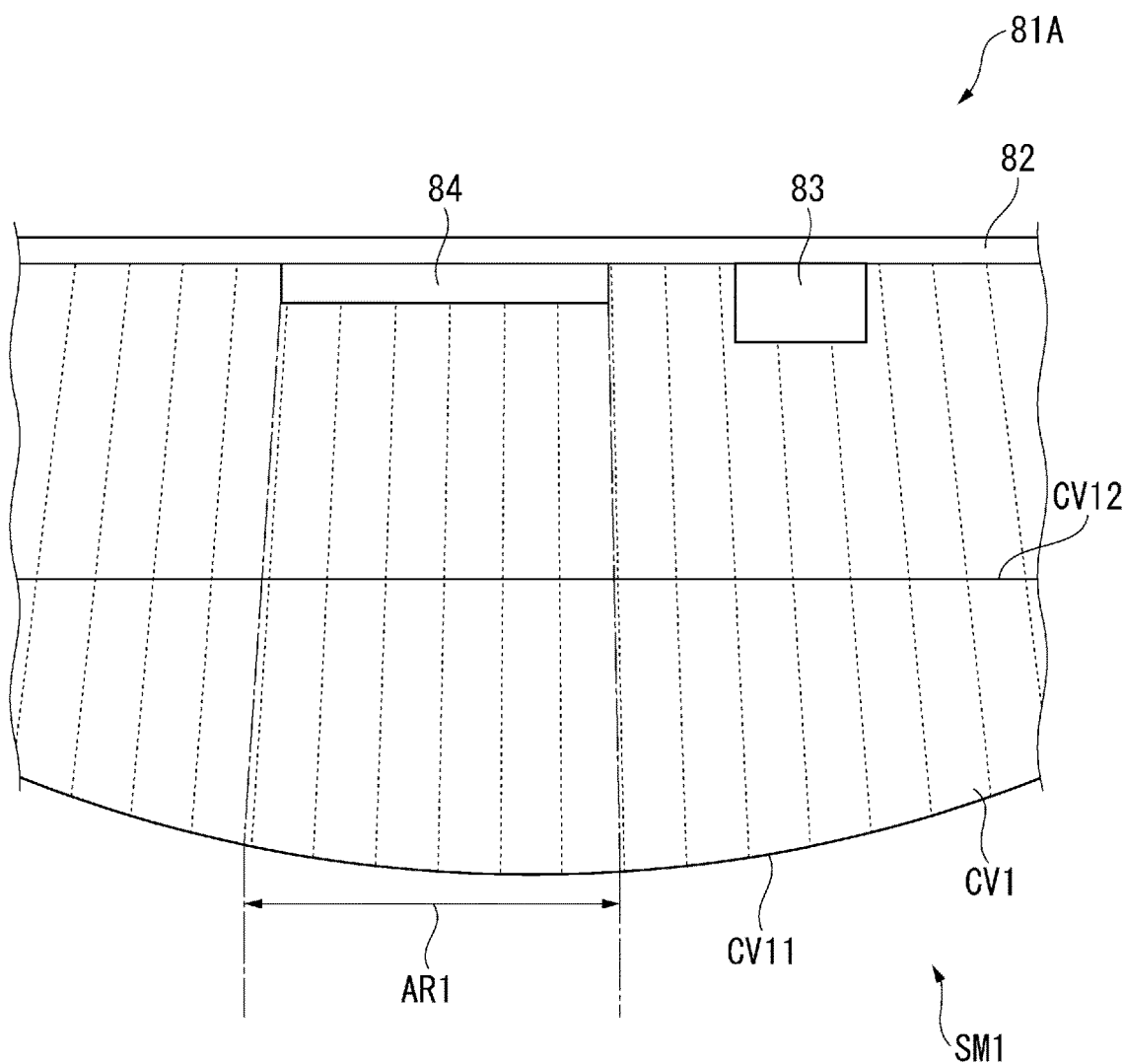
FIG. 5 is a diagrammatic view showing the optical path of second light in Comparative Example of the first embodiment.

Optical Path in a Case where a Passage Section Having No Second Convex Curved Surface is Employed FIG. 5 shows Comparative Example of the biological sensor module 8A and is a diagrammatic view showing the optical path of the second light passing through a biological sensor module SM1 including a passage section CV1 having no second convex curved surface in place of the passage section 86A. In FIG. 5, the light blocker 85 is omitted.

The second light passing through the biological sensor module SM1, which is Comparative Example of the biological sensor module 8A, will be described.

The biological sensor module SM1 has the same configuration as that of the biological sensor module 8A except that the passage section 86A is replaced with the passage section CV1 having no second convex curved surface.

The passage section CV1 is formed in a one-side convex shape having a convex curved surface CV11, which is similar to the first convex curved surface 871, and a flat surface CV12, which is opposite the convex curved surface CV11.

The convex curved surface CV11 is so designed as to have a shape capable of exerting predetermined pressing force on the user's body, as the first convex curved surface 871, but does not have high ability to collect incident light into a spot on the light receiver 84. Therefore, the second light incident on the convex curved surface CV11 is refracted at the flat surface CV12 but travels substantially straight and passes through the passage section CV1. Therefore, out of an area of the convex curved surface CV11 that is the area on which the second light is incident, a light incident area AR1, on which the second light passing through the passage section CV1 and incident on the light receiver 84 is incident, is slightly greater than the area that overlaps with the light receiver 84 in the plan view.

Figure 6:
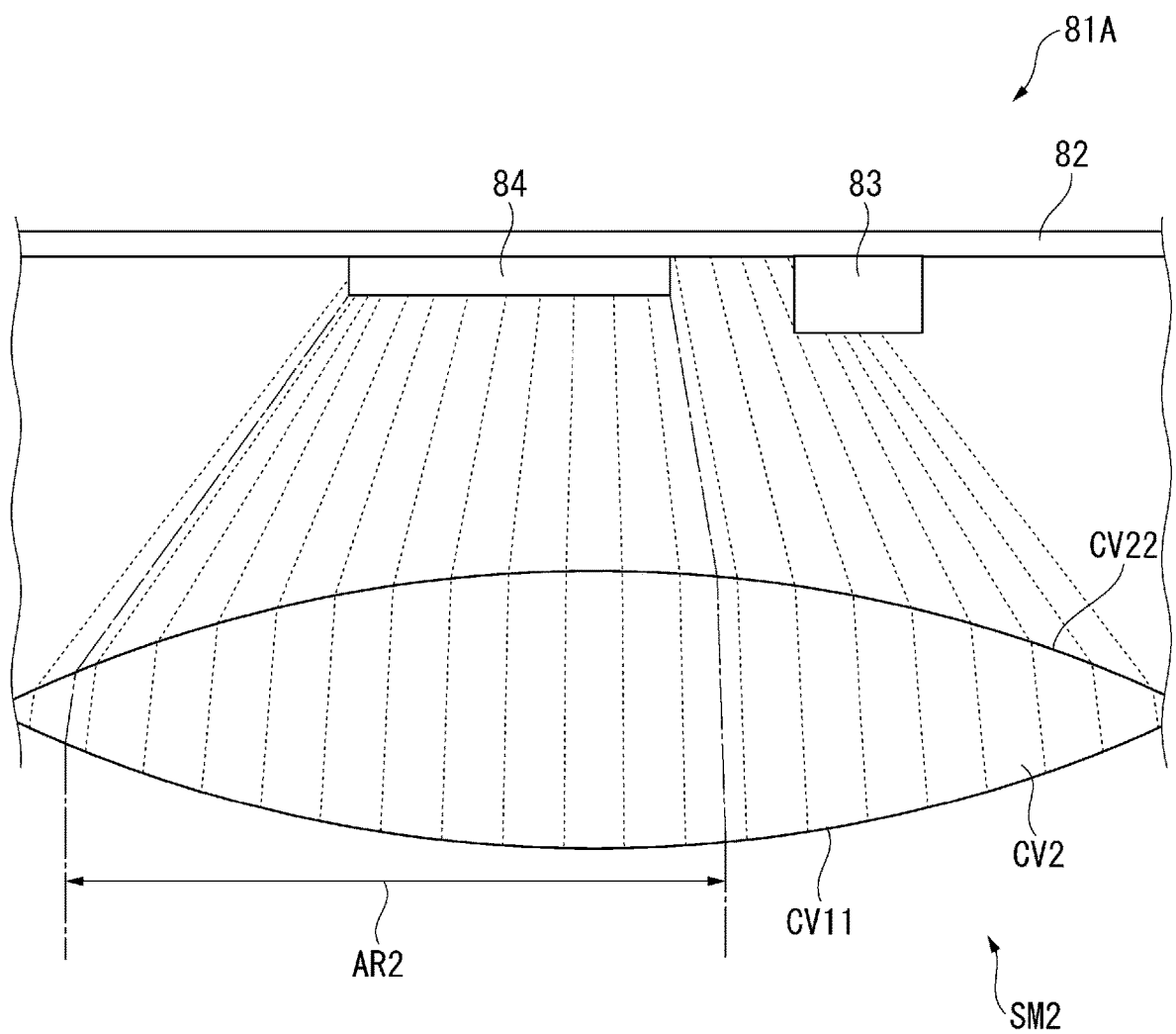
FIG. 6 is a diagrammatic view showing the optical path of the second light in Comparative Example of the first embodiment.

Optical Path in a Case where a Passage Section Having a Second Convex Curved Surface Having a Radius of Curvature Equal to that of the First Convex Curved Surface is Employed FIG. 6 shows Comparative Example of the biological sensor module 8A and is a diagrammatic view showing the optical path of the second light passing through a biological sensor module SM2 including a passage section CV2 having a biconvex shape in place of the passage section 86A.

The biological sensor module SM2 shown in FIG. 6 is Comparative Example of the biological sensor module 8A and has the same configuration as that of the biological sensor module 8A except that the passage section 86A is replaced with the passage section CV2.

The passage section CV2 is formed in a biconvex shape having the convex curved surface CV11 and a convex curved surface CV22, which is opposite the convex curved surface CV11 and protrudes toward the negative side in the direction Z.

The convex curved surface CV22 has a radius of curvature equal to that of the convex curved surface CV11. The convex curved surface CV22 therefore does not have very high ability to collect the light passing through the passage section CV2 into a spot on the light receiver 84. However, in regard to the passage section CV2 as a whole, the light collection performed by the convex curved surfaces CV11 and CV22 causes, out of an area of the convex curved surface CV11 that is the area on which the second light is incident, a light incident area AR2, on which the second light passing through the passage section CV2 and incident on the light receiver 84 is incident, to be greater than the light incident area AR1 described above.

Figure 7:
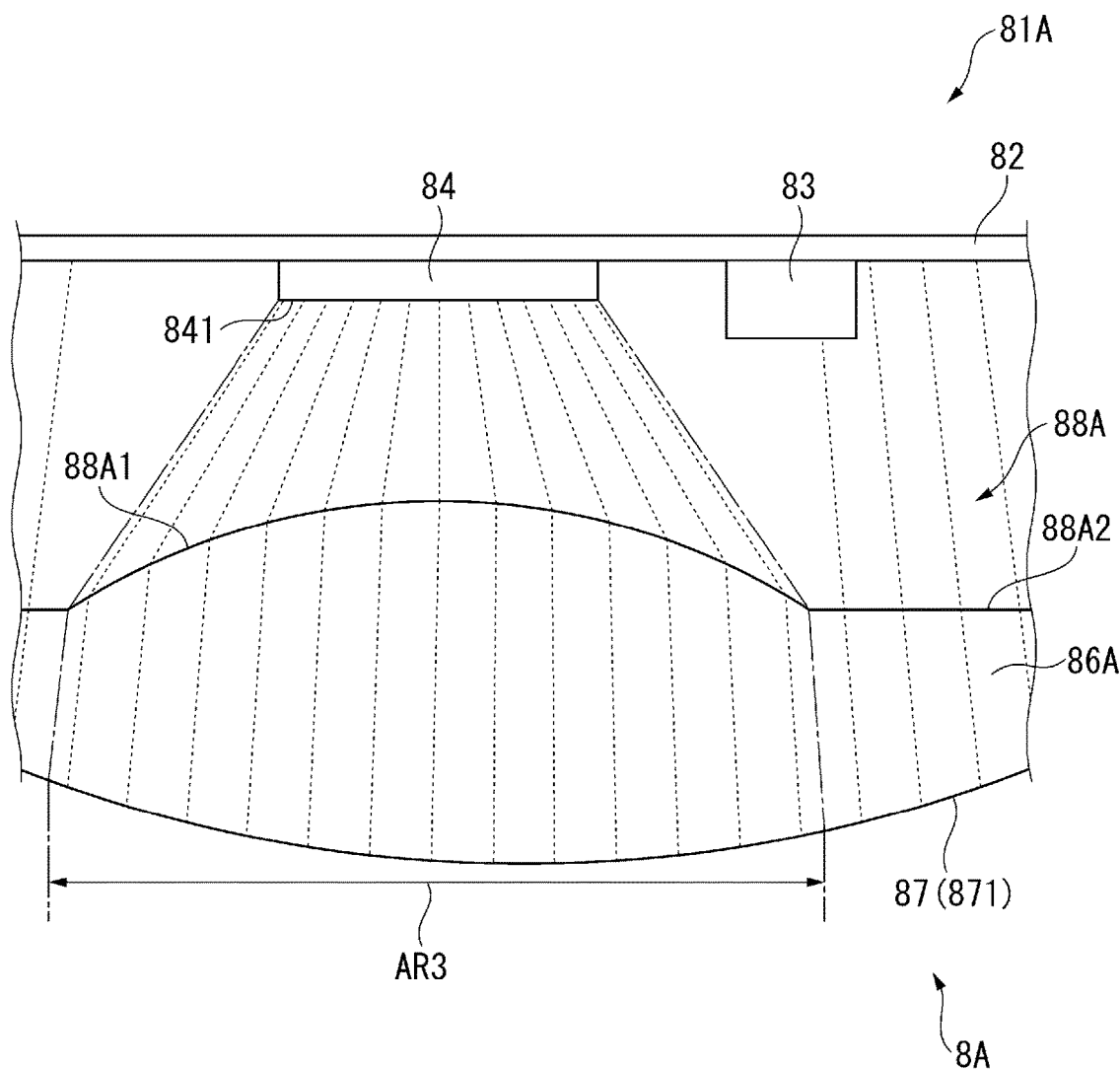
FIG. 7 is a diagrammatic view showing the optical path of the second light in the first embodiment.

Optical Path in a Case where the Passage Section in the Present Embodiment is Employed FIG. 7 is a diagrammatic view showing the optical path of the second light passing through the passage section 86A in the biological sensor module 8A.

In the biological sensor module 8A, the second convex curved surface 88A1 provided in accordance with the light receiver 84 has a radius of curvature smaller than that of the first convex curved surface 871. The second convex curved surface 88A1 therefore has light collection ability higher than that of each of the flat surface CV12 and the convex curved surface CV22 described above. The center C4 of the second convex curved surface 88A1 in the plan view is so set as to fall within the range described above.

As a result, out of the second light passing through the passage section 86A, not only the second light incident on the portion according to the light receiver 84 in the plan view but the second light incident on a portion outside the light receiver 84 in the plan view are allowed to be incident on the light receiver 84. Therefore, an area of the first convex curved surface 871 that is the area on which the second light is incident, a light incident area AR3, on which the second light passing through the passage section 86A and incident on the light receiver 84 is incident, is greater than the light incident area AR2 described above.

Therefore, in the biological sensor module 8A, the amount of second light received by the light receiver 84 can be increased, as compared with the amount in Comparative Example described above, whereby the biological information measuring apparatus 1A can detect biological information with increased precision.

The amount of second light reflected off the user's body and incident on the passage section 86A is greater in an area closer to the light emitter 83 with respect to the light receiver 84 than in an area opposite the light emitter 83 with respect to the light receiver 84. An outer-edge portion of the second convex curved surface 88A1 refracts incident light by a greater amount than a central portion of the second convex curved surface 88A1. Adjusting the position of the center C4 of the second convex curved surface 88A1 and the outer diameter of the second convex curved surface 88A1, which functions as a light collection lens, in such a way that an outer-edge portion of the second convex curved surface 88A1 viewed from the positive side in the direction Z can pick up the reflected light originating from the periphery of the light emitter 83 can further increase the amount of second light incident on the light receiver 84 and in turn the amount of second light received by the light receiver 84.

That is, in the state in which the radius of curvature of the second convex curved surface 88A1 is set to be smaller than the radius of curvature of the first convex curved surface 871 and the center C4 of the second convex curved surface 88A1 in the plan view is so set as to fall within the range described above, adjusting the positional relationship between the outer edge of the second convex curved surface 88A1 and the light emitter 83 and the outer diameter of the second convex curved surface 88A1, for example, disposing the second convex curved surface 88A1 in such a way that the outer edge of the second convex curved surface 88A1 overlaps with the light emitter 83 can further increase the amount of second light, which is originally the first light, which is the illumination light emitted from the light emitter 83, and is the light reflected off the living body.

Effects Provided by First Embodiment

The biological information measuring apparatus 1A according to the present embodiment described above provides the following effects.

The biological sensor module 8A includes the light emitter 83, which emits the first light toward the user's body, which is a living body, the light receiver 84, which receives the second light incident from the user's body, and the passage section 86A, through which the first light and the second light pass. The passage section 86A includes the outer surface section 87, which comes into contact with the user's body, and the inner surface section 88A, which is opposite the outer surface section 87. The outer surface section 87 has the first convex curved surface 871, which presses the user's body, and the inner surface section 88A has the second convex curved surface 88A1, which collects the second light incident on the passage section 86A into a spot on the light receiver 84. In a cross section parallel to the plane XZ, the radius of curvature of the second convex curved surface 88A1 is smaller than the radius of curvature of the first convex curved surface 871.

The configuration described above allows the first convex curved surface 871 of the outer surface section 87 to apply extra-blood-vessel pressure substantially equal to the intra-blood-vessel pressure to the user's body. The change in the volume of the blood vessel can therefore be increased, whereby the change in the detection signal based on the amount of second light reflected off the blood vessel and received by the light receiver 84 can be increased. The pulse wave, which is one piece of biological information, can therefore be detected based on the detection signal with increased precision, whereby the S/N ratio of the pulse signal can be increased.

The amount by which the second light incident on the second convex curved surface 88A1 of the inner surface section 88A is refracted is greater than the amount by which the second light incident on the first convex curved surface 871 is refracted, and the refracted second light travels toward the light receiver 84. The amount of second light received by the light receiver 84 can thus be increased. The pulse wave, which is one piece of biological information, can therefore be detected based on the detection signal with increased precision, whereby the S/N ratio of the pulse signal can be increased.

The biological information measuring apparatus 1A includes the biological sensor module 8A, the housing 2, in which the biological sensor module 8A is provided, and the processing section 7, which calculates the pulse rate, which is one piece of biological information, based on the detection signal outputted from the light receiver 84. Therefore, since the detection signal outputted from the light receiver 84 of the biological sensor module 8A changes by a large amount, the processing section 7 can calculate the pulse rate, which is one piece of biological information, with increased precision.

The center C4 of the second convex curved surface 88A1 is so set as to fall within the range including the center C3 of the light receiver 84 and the center C1 of the first convex curved surface 871 and between the center C3 of the light receiver 84 and the center C1 of the first convex curved surface 871 in the plan view. The second convex curved surface 88A1 can therefore be so located that the second light, which is originally the first light emitted from the light emitter 83 and reflected off the user's body, is efficiently incident on the light receiver 84 via the passage section 86A.

The second convex curved surface 88A1 has the portion that does not overlap with the light receiver 84 in the plan view. Therefore, not only the second light incident on a portion of the second convex curved surface 88A1 that is the portion that overlaps with the light receiver 84 but the second light incident on a portion of the second convex curved surface 88A1 that is the portion that does not overlap with the light receiver 84 are allowed to travel toward the light receiver 84. The amount of second light received by the light receiver 84 can thus be further increased, whereby the pulse wave can be detected with further increased precision.

The rear surfaces section 22 of the housing 2 includes the contact section 221, in which the opening 222, in which the passage section 86A is disposed, is formed and which comes into contact with the user's body. The center C1 of the first convex curved surface 871 coincides with the center of the contact section 221 in the plan view. The housing 2 is therefore so configured that the first convex curved surface 871 can press the user's body at the center of the contact section 221, which comes into contact with the user's body. The pressing force can therefore be effectively exerted on the user's body.

Variation of First Embodiment

In the biological sensor module 8A, the second convex curved surface 88A1 is so formed over a range of the inner surface section 88A of the passage section 86A as to overlap with the light emitter 83 and the light receiver 84 in the plan view, but not necessarily. The range over which the second convex curved surface is formed can be changed as appropriate as long as the second convex curved surface is so formed as to have an area that overlaps with at least part of the light receiver 84 in the plan view and an area that does not overlap with the light receiver 84 in the plan view.

In the following description, the same or substantially the same portion having been already described has the same reference character and will not be described.

Figure 8:
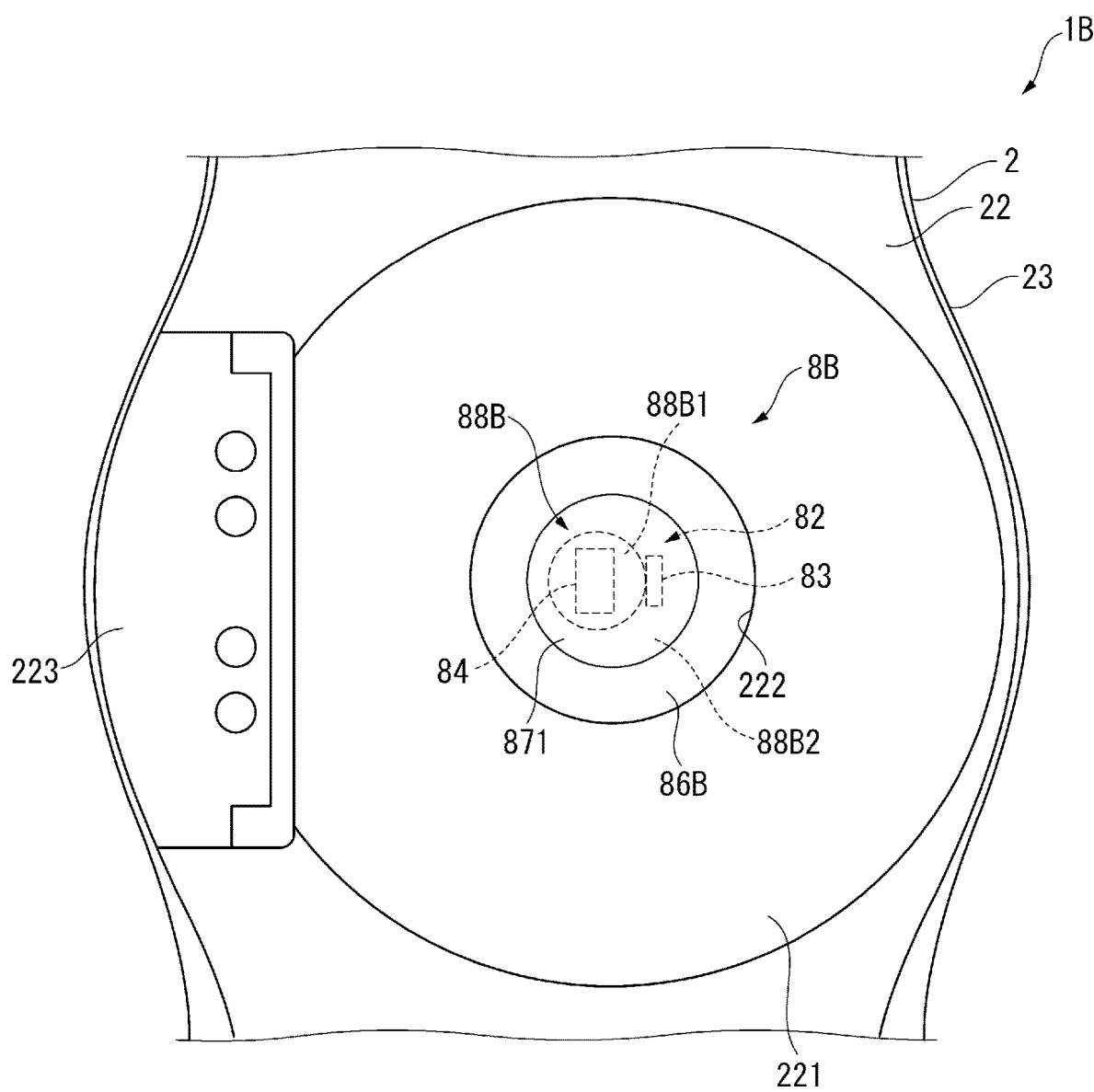
FIG. 8 is a plan view showing the rear surface section provided with a biological sensor module that is a variation of the first embodiment.

FIG. 8 is a plan view showing the rear surface section 22 provided with a biological sensor module 8B, which is a variation of the biological sensor module 8A.

For example, the biological sensor module 8B shown in FIG. 8 has the same configuration and function of the biological sensor module 8A except that the passage section 86A is replaced with a passage section 86B.

The passage section 86B includes the outer surface section 87 and an inner surface section 88B, which is opposite the outer surface section 87, and the inner surface section 88B has a second convex curved surface 88B1 and a flat surface 88A2. A flat surface 88B2 is located in an area of the inner surface section 88B that is the area other than a second convex curved surface 88B1.

The second convex curved surface 88B1 is formed in a substantially circular shape over a range that overlaps with the light receiver 84 and an area outside the light receiver 84 but does not overlap with the light emitter 83 in the plan view.

Also in this case, the radius of curvature of the second convex curved surface 88B1 in a cross section parallel to the plane XZ is smaller than the radius of curvature of the first convex curved surface 871. The center C4 of the second convex curved surface 88B1 is so set as to fall within the same range as in the case of the second convex curved surface 88A1. The center C1 of the first convex curved surface 871 coincides with the center of the contact section 221 provided in the rear surface section 22 in the plan view also in the case of the housing 2 in which the biological sensor module 8B is provided.

A biological information measuring apparatus 1B including the thus configured biological sensor module 8B can also provide the same effects as those provided by the biological information measuring apparatus 1A including the biological sensor module 8A.

Second Embodiment

A second embodiment of the present disclosure will next be described.

A biological information measuring apparatus according to the present embodiment has the same configuration as those of the biological information measuring apparatuses 1A and 1B shown in the first embodiment. The biological information measuring apparatus according to the present embodiment, however, differs from the biological information measuring apparatuses 1A and 1B in that the biological sensor module includes a plurality of light emitters 83 and the second convex curved surface is formed of a plurality of curved surface sections according to the plurality of light emitters. In the following description, the same or substantially the same portion having been already described has the same reference character and will not be described.

Figure 9:
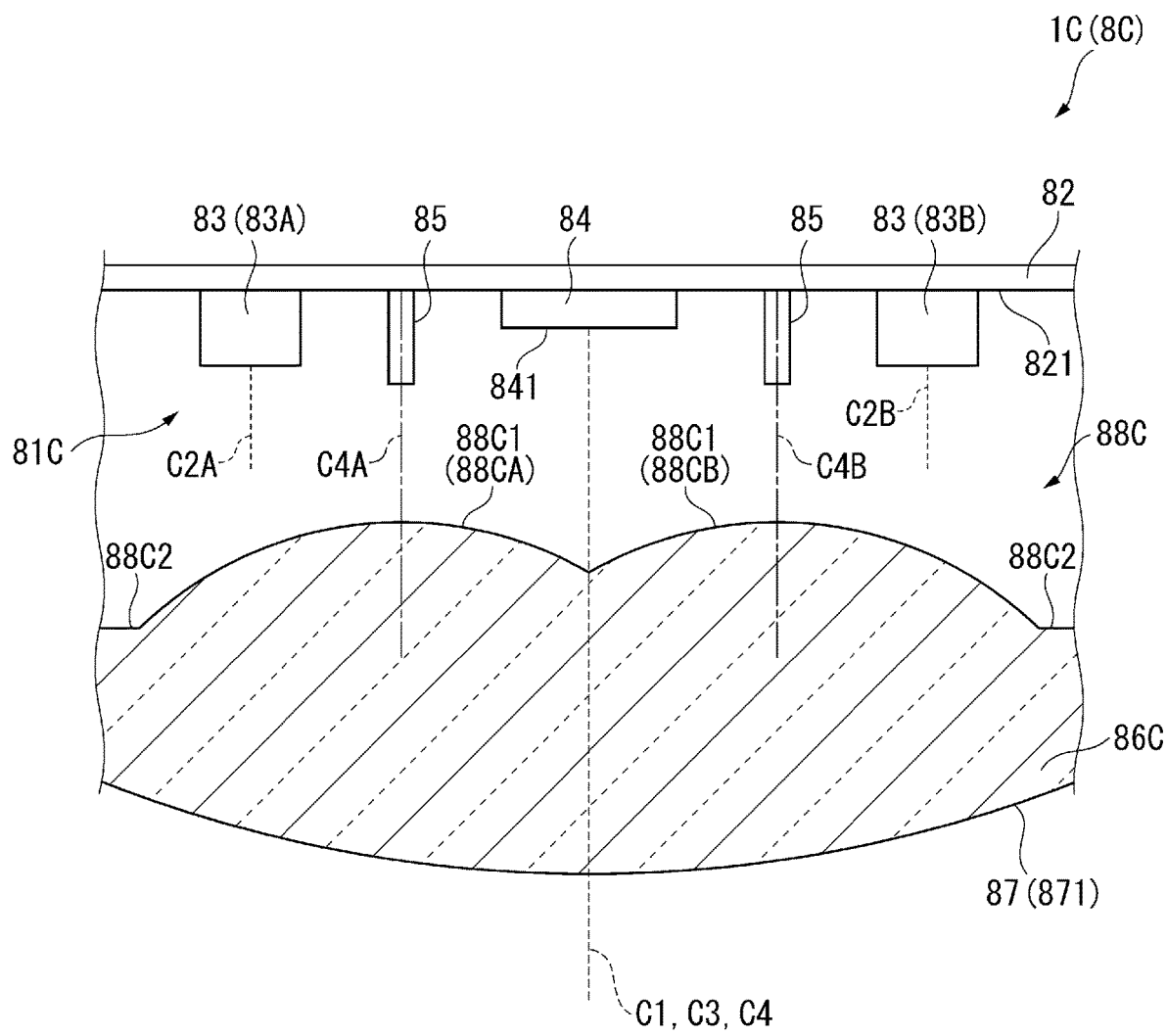
FIG. 9 is a cross-sectional view showing a biological sensor module provided in a biological information measuring apparatus according to a second embodiment of the present disclosure.

FIG. 9 is a cross-sectional view showing a biological sensor module 8C provided in a biological information measuring apparatus 1C according to the present embodiment. In detail, FIG. 9 shows the cross section of the biological sensor module 8C taken along a plane parallel to the plane XZ.

The biological information measuring apparatus 1C according to the present embodiment has the same configuration and function as those of the biological information measuring apparatus 1A except that the biological sensor module 8A is replaced with the biological sensor module 8C.

The biological sensor module 8C detects biological information from the user's body, which is a living body, as the biological sensor module 8A does. The biological sensor module 8C includes a sensor section 81C and a passage section 86C, as shown in FIG. 9.

The sensor section 81C includes the substrate 82, two light emitters 83 (83A and 83B), one light receiver 84, and a light blocker 85, which are provided on the substrate 82. The light emitters 83A and 83B, the light receiver 84, and the light blocker 85 are disposed in the opening 222 in the plan view.

The two light emitters 83A and 83B are provided on the surface 821 of the substrate 82 in positions that sandwich the one light receiver 84 in the direction +X. Specifically, the light emitter 83A is disposed in a position shifted from the light receiver 84 toward the negative side in the direction X, and the light emitter 83B is disposed in a position shifted from the light receiver 84 toward the positive side in the direction X. A center C2A of the light emitter 83A, a center C2B of the light emitter 83B, and the center C3 of the light receiver 84 are located along an imaginary straight line in the plan view.

The inter-center distance between the light emitter 83A and the light receiver 84 may be equal to or may differ from the inter-center distance between the light emitter 83B and the light receiver 84. The wavelength of the light emitted from the light emitter 83A may be equal to or may differ from the wavelength of the light emitted from the light emitter 83B. Further, the light emitters 83A and 83B are not necessarily turned on at the same time, and in the period for which one of the light emitters emits light, the other may not emit light.

The light receiver 84 receives second light that is originally the first light emitted from at least one of the light emitters 83A and 83B and incident from the user's body via the passage section 86C. In the present embodiment, the light receiver 84 is disposed at the center of the contact section 221 (see FIG. 3).

The light blocker 85 is formed in a frame-like shape that surrounds the light receiver 84 in the plan view although not shown and is located between the light emitters 83A/83B and the light receiver 84.

The passage section 86C is a light transmissive member that is fit into the opening 222 to protect the sensor section 81C disposed in the housing 2 and transmits the first light emitted from the light emitters 83A and 83B and the second light to be incident on the light receiver 84, as the passage sections 86A and 86B are. The passage section 86C includes the outer surface section 87, which is located on the positive side in the direction Z, and an inner surface section 88C, which is opposite the outer surface section 87 and faces the light emitters 83A and 83B and the light receiver 84.

The center C1 of the first convex curved surface 871 of the outer surface section 87 substantially coincides with the center of the contact section 221 in the plan view, as described above. In the present embodiment, the center C1 is set at the center of an imaginary minimum circle containing the light emitters 83A and 83B and the light receiver 84 in the plan view. In the present embodiment, the center C1 of the first convex curved surface 871 coincides with the center C3 of the light receiver 84, and the center C3 of the light receiver 84 coincides with the center of the imaginary minimum circle.

The inner surface section 88C has a second convex curved surface 88C1 and a flat surface 88C2, which is an area of the inner surface section 88C that is the area other than the second convex curved surface 88C1.

The second convex curved surface 88C1 protrudes toward the negative side in the direction Z and collects the second light incident thereon into spots on the light receiver 84. The second convex curved surface 88C1 includes a curved surface section 88CA, which has a center C4A located between the center C2A of the light emitter 83A and the center C3 of the light receiver 84 in the plan view, and a curved surface section 88CB, which has a center C4B located between the center C2B of the light emitter 83B and the center C3 of the light receiver 84 in the plan view. The center C4 of the entire second convex curved surface 88C1 coincides with the centers C1 and C3 in the plan view.

The curved surface section 88CA is so formed as to overlap with part of each of the light emitter 83A and the light receiver 84 in the plan view. In other words, the curved surface section 88CA includes an area that overlaps with the light receiver 84 and an area that does not overlap with the light receiver 84 in the plan view. The curved surface section 88CA collects the second light that is originally the first light emitted from the light emitter 83A into a spot on the light receiver 84.

The curved surface section 88CB is so formed as to overlap with part of each of the light emitter 83B and the light receiver 84. In other words, the curved surface section 88CB also includes an area that overlaps with the light receiver 84 and an area that does not overlap with the light receiver 84 in the plan view. The curved surface section 88CB collects the second light that is originally the first light emitted from the light emitter 83B into a spot on the light receiver 84.

The radii of curvature of the curved surface sections 88CA and 88CB in a cross section parallel to the plane XZ are equal to each other and smaller than the radius of curvature of the first convex curved surface 871.

The center C4 of the entire second convex curved surface 88C1 coincides with the center C1 of the first convex curved surface 871 and the center C3 of the light receiver 84 in the plan view.

The biological information measuring apparatus 1C according to the present embodiment described above can also provide the same effects as those provided by the biological information measuring apparatus 1A.

That is, the second convex curved surface 88C1 including the curved surface sections 88CA and 88CB allows the second light that is originally the first light emitted from the light emitters 83A and 83B and incident from the user's body to be readily incident on the light receiver 84. The amount of second light received by the light receiver 84 can therefore be increased.

Variation of Second Embodiment

In the biological sensor module 8C, the second convex curved surface 88C1 of the passage section 86C has a shape that is the combination of the two convex curved surfaces, that is, the curved surface sections 88CA and 88CB, but not necessarily. The shape of the second convex curved surface can be changed as appropriate.

For example, in a case where three or more light emitter 83 are so provided as to surround the light receiver 84, curved surface sections that form the second convex curved surface may be provided in accordance with the light emitters 83.

Figure 10:
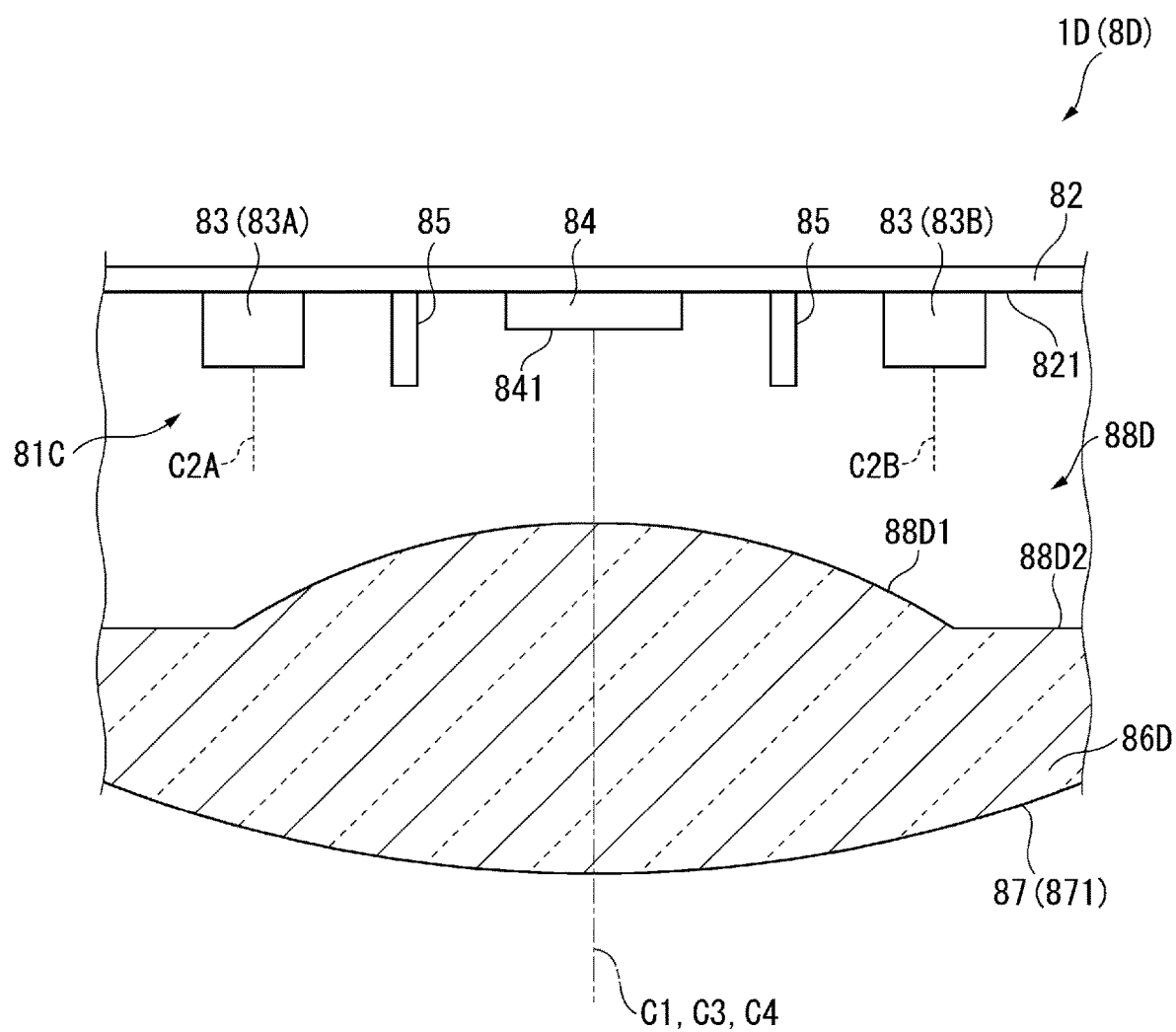
FIG. 10 is a cross-sectional view showing a biological sensor module that is a variation of the second embodiment.

FIG. 10 is a cross-sectional view showing a biological sensor module 8D, which is a variation of the biological sensor module 8C. Specifically, FIG. 10 shows the cross section of the biological sensor module 8D taken along the plane XZ.

The second convex curved surface may be formed of one curved surface section irrespective of the number of light emitters 83, as the second convex curved surface 88A1 is.

For example, the biological information measuring apparatus 1C may employ the biological sensor module 8D shown in FIG. 10 in place of the biological sensor module 8C. The biological sensor module 8D has the same configuration and function as those of the biological sensor module 8C except that the passage section 86C is replaced with a passage section 86D.

The passage section 86D includes the outer surface section 87 and an inner surface section 88D, which is opposite the outer surface section 87 and faces the light emitters 83A and 83B, the light receiver 84, and the light blocker 85.

The center C1 of the first convex curved surface 871 of the outer surface section 87 coincides with the center of the contact section 221 and the center C3 of the light receiver 84, as described above.

The inner surface section 88D has a second convex curved surface 88D1, which protrudes toward the negative side in the direction Z, and a flat surface 88D2, which is perpendicular to the direction +Z, as the flat surface 88A2 is. The second convex curved surface 88D1 is formed of one curved surface section that protrudes toward the negative side in the direction Z with the amount of protrusion increasing with distance toward the center of the second convex curved surface 88D1 in the plan view, unlike the second convex curved surface 88C1. That is, the second convex curved surface 88D1 is a continuous convex curved surface having a single radius of curvature and is formed in a substantially circular shape in the plan view.

The center C4 of the second convex curved surface 88D1 in the plan view coincides with the center C2 of the light receiver 84. The range over which the second convex curved surface 88D1 is formed is a range that overlaps with the entire light receiver 84 in the plan view. That is, the second convex curved surface 88D1 has an area that overlaps with the entire light receiver 84 having an oblong shape in the plan view and an area that does not overlap with the light receiver 84 in the plan view. The range over which the second convex curved surface 88D1 is formed may further contain at least part of at least one of the light emitters 83A and 83B.

In the thus configured biological sensor module 8D, the second light that is not incident on the light receiver 84 if no second convex curved surface 88D1 is present is allowed to be incident on the light receiver 84 by causing the second light to pass through the second convex curved surface 88D1. The amount of second light received by the light receiver 84 can thus be increased.

The biological information measuring apparatus 1D including the thus configured biological sensor module 8D can therefore also provide the same effects as those provided by the biological information measuring apparatus 1C.

Third Embodiment

A third embodiment of the present disclosure will next be described.

A biological information measuring apparatus according to the present embodiment has the same configuration as those of the biological information measuring apparatuses 1A and 1B shown in the first embodiment. The biological information measuring apparatus according to the present embodiment, however, differs from the biological information measuring apparatuses 1A and 1B in that the biological sensor module includes a plurality of light receivers and the second convex curved surface is formed of a plurality of curved surface sections according to the plurality of light receivers. In the following description, the same or substantially the same portion having been already described has the same reference character and will not be described.

Figure 11:
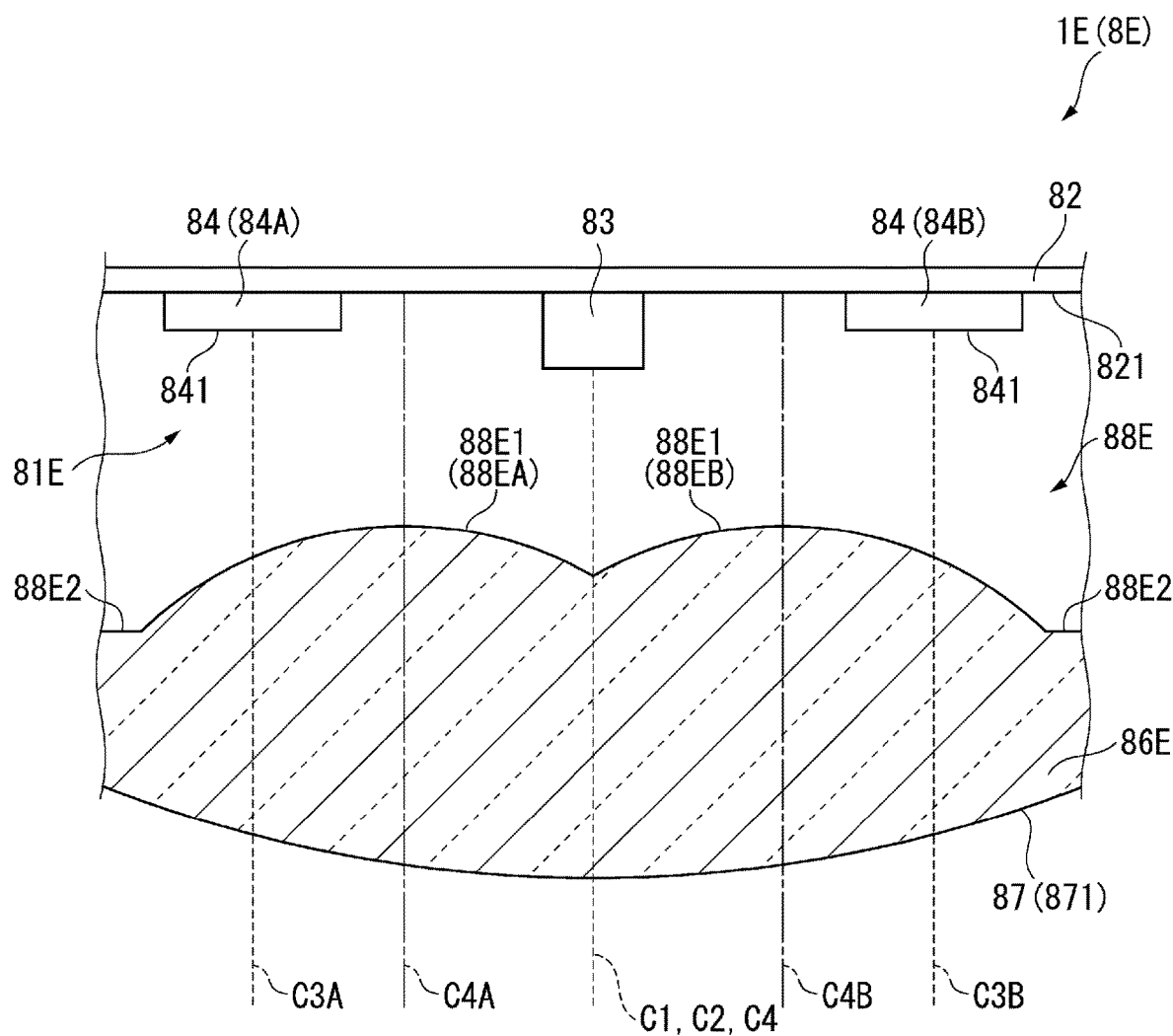
FIG. 11 is a cross-sectional view showing a biological sensor module provided in a biological information measuring apparatus according to a third embodiment of the present disclosure.

FIG. 11 is a cross-sectional view showing a biological sensor module 8E provided in a biological information measuring apparatus 1E according to the present embodiment. In detail, FIG. 11 shows the cross section of the biological sensor module 8E taken along the plane XZ. In FIG. 11, the light blocker 85 is omitted.

The biological information measuring apparatus 1E according to the present embodiment has the same configuration and function as those of the biological information measuring apparatus 1A except that the biological sensor module 8A is replaced with the biological sensor module 8E.

The biological sensor module 8E detects biological information from the user's body, which is a living body. The biological sensor module 8E includes a sensor section 81E and a passage section 86E, as shown in FIG. 11.

The sensor section 81E includes the substrate 82, one light emitter 83, two light receivers 84 (84A and 84B), and a light blocker 85 (not shown), which are provided on the substrate 82.

The light emitter 83 is disposed at the center of the contact section 221 in the plan view in the biological information measuring apparatus 1E.

The two light receivers 84A and 84B are disposed in positions that sandwich the light emitter 83 in the direction +X. Specifically, the light receiver 84A is disposed in a position shifted from the light emitter 83 toward the negative side in the direction X, and the light receiver 84B is disposed in a position shifted from the light emitter 83 toward the positive side in the direction X. A center C3A of the light receiver 84A, a center C4B of the light receiver 84B, and the center C2 of the light emitter 83 are located along an imaginary straight line in the plan view.

The inter-center distance between the light receiver 84A and the light emitter 83 may be equal to or may differ from the inter-center distance between the light receiver 84B and the light emitter 83.

The passage section 86E is a light transmissive member that is fit into the opening 222 to protect the sensor section 81E and transmits the first light emitted from the light emitter 83 and the second light to be received by the light receivers 84A and 84B.

The passage section 86E includes the outer surface section 87 and an inner surface section 88E, which is opposite the outer surface section 87 and faces the light emitter 83 and the light receivers 84A and 84B.

The inner surface section 88E has a second convex curved surface 88E1 and a flat surface 88E2, which is the area other than the second convex curved surface 88E1, as the second convex curved surface 88C does.

The second convex curved surface 88E1 is the combination of curved surface sections 88EA and 88EB, which are convex curved surfaces that protrude toward the negative side in the direction Z in accordance with the light receivers 84A and 84B.

The curved surface section 88EA collects the second light incident on the area facing the light receiver 84A out of the second light incident from the user's body on the passage section 86E. The curved surface section 88EA includes an area that overlaps with at least part of the light receiver 84A and an area that does not overlap with the light receiver 84A in the plan view, for example, an area between the light receiver 84A and the light emitter 83.

In the plan view, the center C4A of the curved surface section 88EA is so set as to fall within the range including the center C3A of the light receiver 84A and between the center C3A and the center C2 of the light emitter 83. The thus configured curved surface section 88EA can increase the amount of second light received by the light receiver 84A.

The curved surface section 88EB collects the second light incident on the area facing the light receiver 84B out of the second light incident from the user's body on the passage section 86E. The curved surface section 88EB includes an area that overlaps with at least part of the light receiver 84B and an area that does not overlap with the light receiver 84B in the plan view, for example, an area between the light receiver 84B and the light emitter 83.

In the plan view, the center C4B of the curved surface section 88EB is so set as to fall within the range including the center C3B of the light receiver 84B and between the center C3B and the center C2 of the light emitter 83. The thus configured curved surface section 88EB can increase the amount of second light received by the light receiver 84B.

The center C4 of the second convex curved surface 88E1, which is formed of the curved surface sections 88EA and 88EB, in the plan view coincides with the center C1 of the first convex curved surface 871, which coincides with the center of the contact section 221 in the plan view, and the center C2 of the light emitter 83.

The biological information measuring apparatus 1E according to the present embodiment described above can provide the same effects as those provided by the biological information measuring apparatus 1A.

The number of curved surface sections that form the second convex curved surface may be changed as appropriate. For example, the inner surface section of the passage section may be provided with a second convex curved surface formed of a single curved surface section that overlaps with at least part of each of the light receivers 84A and 84B in the plan view, as in the case of the second convex curved surface 88D1. The center of the second convex curved surface in the plan view in this case can be so set as to be located between the center of the light receiver 84A and the center of the light receiver 84B, for example, the position where the center of the second convex curved surface coincides with the center C2 of the light emitter 83.

The number of light receivers 84 provided in the sensor section 81E is not limited to two and may instead be three or more. Also in this case, curved surface sections that form the second convex curved surface may be provided in accordance with the light receivers 84, or the inner surface section may be provided with a single second convex curved surface in accordance with two or more light receivers 84.

Further, the plurality of curved surface sections that form the second convex curved surface 88E1 may be so formed as to be separate from each other.

Fourth Embodiment

A fourth embodiment of the present disclosure will next be described.

A biological information measuring apparatus according to the present embodiment has the same configuration as that of the biological information measuring apparatus 1C described above but differs therefrom in terms of the configuration of the passage section. In the following description, the same or substantially the same portion having been already described has the same reference character and will not be described.

Figure 12:
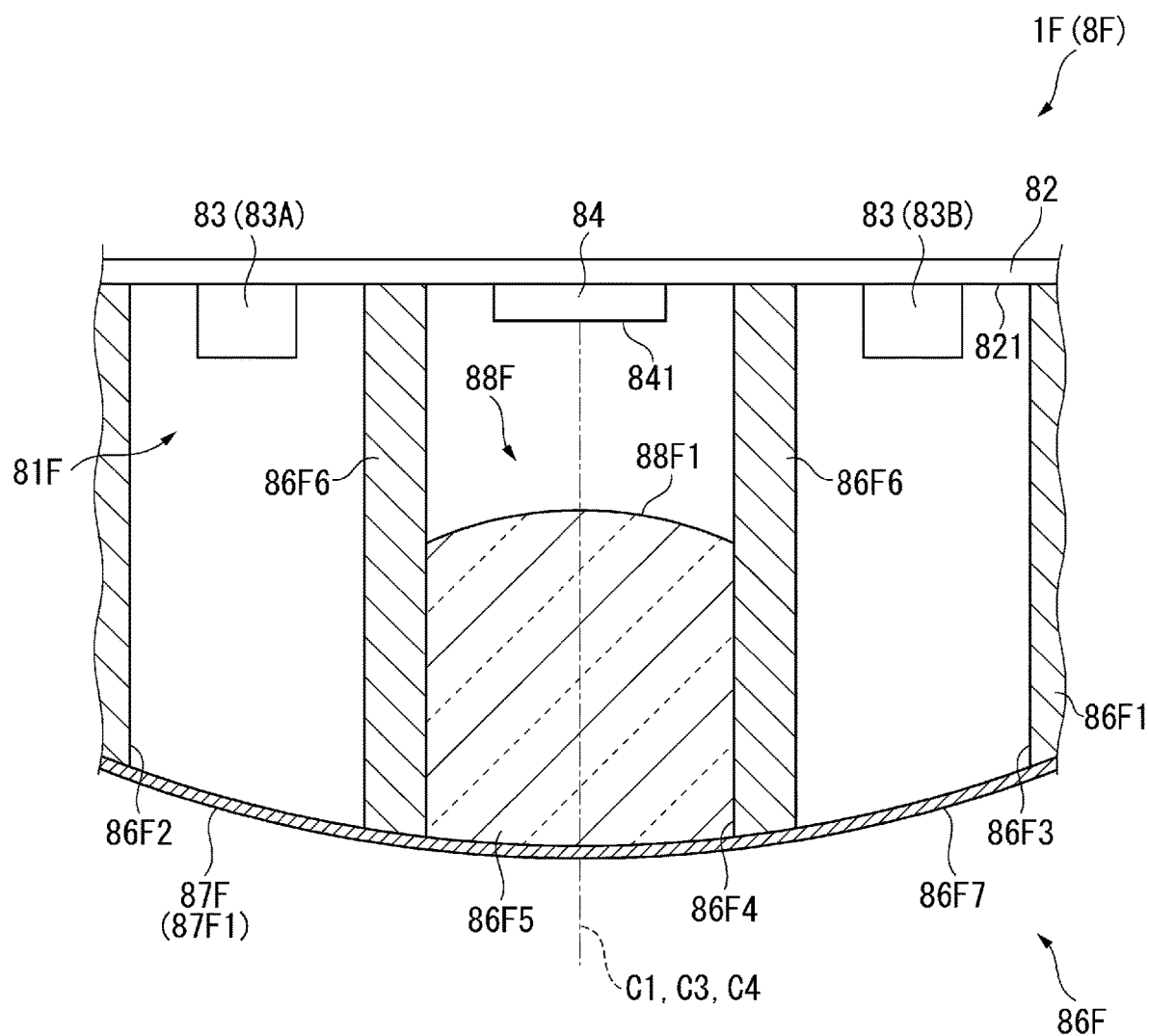
FIG. 12 is a cross-sectional view showing a biological sensor module provided in a biological information measuring apparatus according to a fourth embodiment of the present disclosure.

FIG. 12 is a cross-sectional view showing a biological sensor module 8F provided in a biological information measuring apparatus 1F according to the present embodiment. In detail, FIG. 12 shows the cross section of the biological sensor module 8F taken along the plane XZ.

The biological information measuring apparatus 1F according to the present embodiment has the same configuration and function as those of the biological information measuring apparatus 1A except that the biological sensor module 8A is replaced with the biological sensor module 8F.

The biological sensor module 8F detects the pulse wave, which is the biological information, from the user's body, which is a living body. The biological sensor module 8F includes a sensor section 81F and a passage section 86F, as shown in FIG. 12.

The sensor section 81F has the same configuration and function as those of the sensor section 81C described above except that no light blocker 85 is provided. That is, the sensor section 81F includes the substrate 82, the light emitters 83A and 83B and the light receiver 84, which are provided on the substrate 82.

The passage section 86E is a member that protects the sensor section 81F and transmits the first light emitted from the light emitters 83A and 83B and the second light to be incident on the light receiver 84. The passage section 86F includes a main body section 86F1 and a sheet 86F7, which is attached to the main body section 86F1.

The main body section 86F1 is made of a material that transmits no light, that is, a light blocking material, formed in a substantially circular shape in the plan view, and disposed in the opening 222. The main body section 86F1 includes an outer surface section 87F, which is located on the positive side in the direction Z, openings 86F2 to 86F4, a light collector 86F5, and a light blocker 86F6.

The outer surface section 87F comes into contact with the user's body via the sheet 86F7 attached to the +Z-direction-side of the outer surface section 87F. The outer surface section 87F has a first convex curved surface 87F1, which protrudes toward the positive side in the direction Z with the amount of protrusion increasing with distance toward the center of the first convex curved surface 87F1 in the plan view and presses the user's body. The center C1 of the first convex curved surface 87F1 in the plan view coincides with the center of the contact section 221 and the center C3 of the light receiver 84 in the plan view.

The sheet 86F7 is a light transmissive sheet and can transmit the first light emitted from the light emitters 83A and 83B and the second light to be received by the light receiver 84.

The openings 86F2 to 86F4 are so formed in a circular shape or a rectangular shape in the plan view as to pass through the main body section 86F1 in the direction +Z.

The openings 86F2 and 86F3 are formed in the positions according to the light emitters 83A and 83B in the plan view. The opening 86F2 allows the first light emitted from the light emitter 83A to pass through and exit out of the passage section 86F via the sheet 86F7. Similarly, the opening 86F3 allows the first light emitted from the light emitter 83B to pass through and exit out of the passage section 86F via the sheet 86F7.

The opening 86F4 is formed in the position according to the light receiver 84 in the plan view and allows the second light incident from the user's body via the sheet 86F7 to pass through the passage section 86F and be incident on the light receiver 84. The opening 86F4 is so formed as to be greater than the light receiver 84 in the plan view, and the light collector 86F5 is provided in the opening 86F4.

The light collector 86F5 is made of a light transmissive resin that transmits at least the second light. The −Z-direction-side portion of the light collector 86F5 forms an inner surface section 88F, which is opposite the outer surface section 87F with respect to the passage section 86F.

The inner surface section 88F has a second convex curved surface 88F1, which protrudes toward the negative side in the direction Z with the amount of protrusion increasing with distance toward the center of the second convex curved surface 88F1 in the plan view.

The second convex curved surface 88F1 has an outer edge connected to the inner end surface of the opening 86F4. The second convex curved surface 88F1 therefore has not only an area that overlaps with the light receiver 84 but an area that does not overlap with the light receiver 84 in the plan view.

In a cross section parallel to the plane XZ, the radius of curvature of the second convex curved surface 88F1 is smaller than the radius of curvature of the first convex curved surface 87F1. The center C4 of the second convex curved surface 88F1 coincides with the center C1 of the first convex curved surface 87F1 and the center C3 of the light receiver 84 in the plan view.

The substantially entire second light having been incident into the opening 86F4 and having passed through the second convex curved surface 88F1 is therefore collected into a spot on the light receiver 84. That is, out of the second light incident on the light collector 86F5, not only the second light incident on the area that overlaps with the light receiver 84 but the second light incident on the area that does not overlap with the light receiver 84 in the plan view are incident on the light receiver 84. The amount of light received by the light receiver 84 can thus be increased.

The light blocker 86F6 is a portion that forms the outer edge of the opening 86F4 in the main body section 86F1 and surrounds the light receiver 84 in the plan view. That is, the light blocker 86F6 is located between the light emitter 83A and the light receiver 84 and between the light emitter 83B and the light receiver 84 and defines the area where the light receiver 84 is disposed. The −Z-direction-side end of the light blocker 86F6 is in contact with the surface 821 of the substrate 82.

Since the main body section 86F1 blocks light, the light blocker 86F6 also blocks light. The light blocker 86F6 therefore prevents the first light emitted from the light emitters 83A and 83B from being directly incident on the light receiver 84 without via the user's body.

The biological information measuring apparatus 1F according to the present embodiment described above can provide the same effects as those provided by the biological information measuring apparatus 1C described above.

In the biological sensor module 8F, the light collector 86F5 is provided in the opening 86F4, in which the light receiver 84 is disposed in the plan view, but the openings 86F2 and 86F3, in which the light emitters 83A and 83B are disposed in the plan view, respectively, have not been described. However, a sealing portion made of a light transmissive resin may be provided also in each of the openings 86F2 and 86F3. The sealing portions may have the functions of diffusing and collecting the light emitted from the light emitters 83A and 83B.

The biological sensor module 8F described above includes the light emitters 83A and 83B and the light receiver 84, but not necessarily. The biological sensor module 8F may instead include the light emitter 83 and the two light receivers 84A and 84B that sandwich the light emitter 83, as the biological sensor module 8E does.

In this case, it is conceivable to employ a configuration in which the light emitter 83 is disposed in the opening 86F4, the light receiver 84A is disposed in the opening 86F2, and the light receiver 84B is disposed in the opening 86F3. It is then conceivable that the light collector 86F5 located in the opening 86F4 is omitted and the light collector 86F5 is provided in each of the openings 86F2 and 86F3. That is, it is conceivable that the second convex curved surface 88F1 is provided in accordance with each of the light receivers 84A and 84B.

In this case, the second light incident into the openings 86F2 and 86F3 can be collected into spots on the light receivers 84A and 84B disposed in the openings 86F2 and 86F3 in the plan view. Also in this configuration, it is preferable that the center of each of the second convex curved surfaces 88F1 is so set as to fall within the range including the center of the corresponding light receiver 84 and between the center of the light receiver 84 and the center of the light emitter 83 in the plan view.

Fifth Embodiment

A fifth embodiment of the present disclosure will next be described.

A biological information measuring apparatus according to the present embodiment has the same configuration as that of the biological information measuring apparatus 1A shown in the first embodiment but differs therefrom in that a recess where the second convex curved surface is located is formed in an inner portion of the inner surface section in the plan view. In the following description, the same or substantially the same portion having been already described has the same reference character and will not be described.

Figure 13:
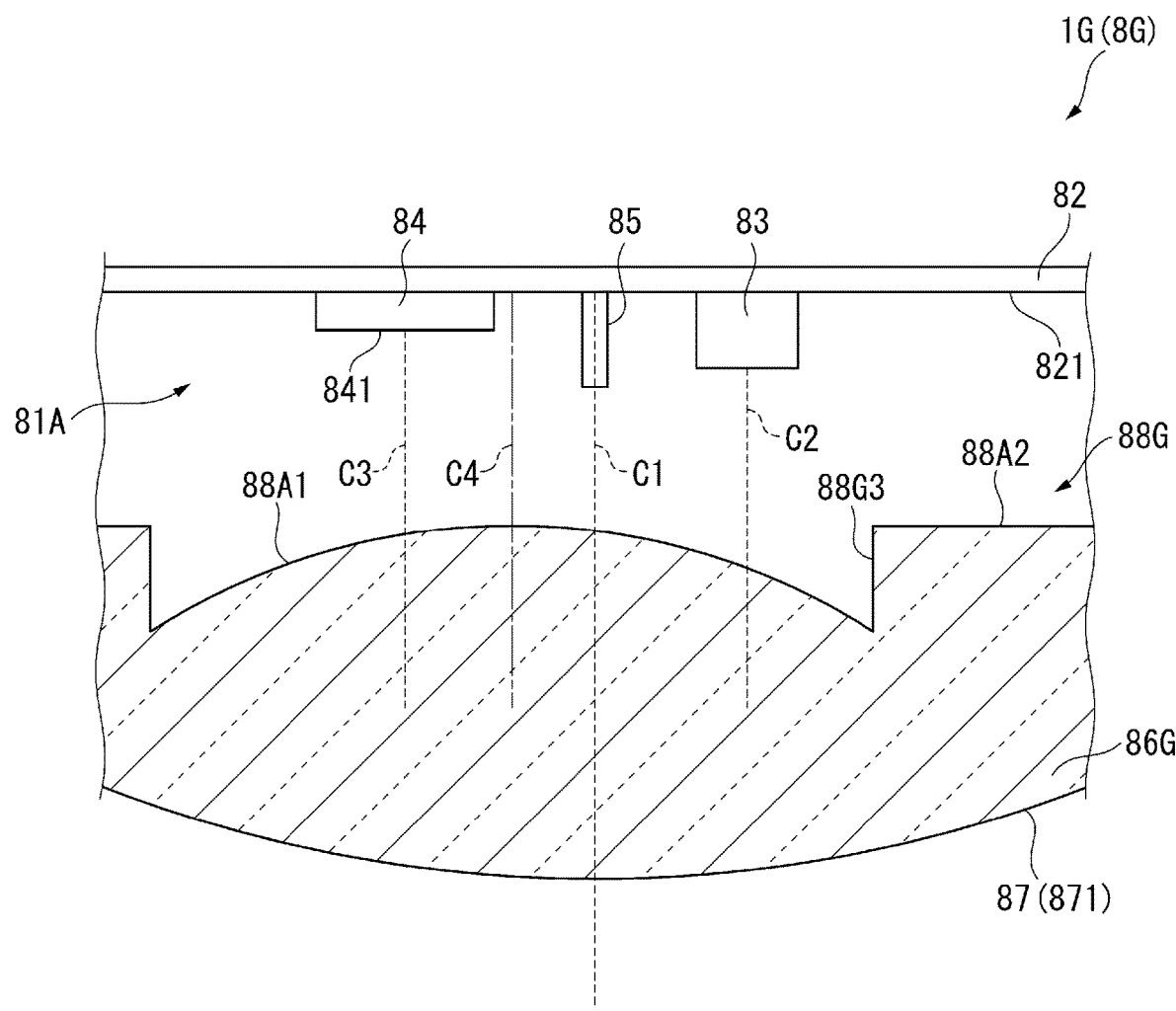
FIG. 13 is a cross-sectional view showing a biological sensor module provided in a biological information measuring apparatus according to a fifth embodiment of the present disclosure.

FIG. 13 is a cross-sectional view showing a biological sensor module 8G provided in a biological information measuring apparatus 1G according to the present embodiment. In detail, FIG. 13 shows the cross section of the biological sensor module 8G taken along the plane XZ.

The biological information measuring apparatus 1G according to the present embodiment has the same configuration and function as those of the biological information measuring apparatus 1A except that the biological sensor module 8A is replaced with the biological sensor module 8G.

The biological sensor module 8G detects the pulse wave, which is the biological information, from the user's body, which is a living body. The biological sensor module 8G includes the sensor section 81A and a passage section 86G, as shown in FIG. 13.

The passage section 86G is a light transmissive member that is fit into the opening 222 to protect the sensor section 81A and transmits the first light emitted from the light emitter 83 and the second light to be received by the light receiver 84.

The passage section 86G includes the outer surface section 87 and an inner surface section 88G, which is opposite the outer surface section 87 and faces the light emitter 83 and the light receiver 84.

The inner surface section 88G has the second convex curved surface 88A1 and the flat surface 88A2 and further includes a recess 88G3, which is recessed toward the positive side in the direction Z. The second convex curved surface 88A1 is located in the recess 88G3 in the plan view, and the flat surface 88A2 is formed in the area outside the recess 88G3.

The center C4 of the second convex curved surface 88A1 in the plan view is so set as to fall within the range including the center C1 of the first convex curved surface 871 and the center C3 of the light receiver 84 and between the center C1 and the center C3. The second convex curved surface 88A1 is so set as to fall within a range containing an area that overlaps with at least part of the light receiver 84 and an area that does not overlap with the light receiver 84.

Effects Provided by Fifth Embodiment

The biological information measuring apparatus 1G according to the present embodiment described above can provide the same effects as those provided by the biological information measuring apparatus 1A and can further provide the following effect.

The inner surface section 88G, which forms the passage section 86G, includes the recess 88G3, which is recessed toward the positive side in the direction Z, which is the second direction from the inner surface section 88G toward the outer surface section 87. The second convex curved surface 88A1 is located in the recess 88G3 in the plan view. The dimension of the passage section 86G in the direction +Z can therefore be reduced with the inner surface section 88G provided with the second convex curved surface 88A1. The thickness of the biological sensor module 8G can therefore be reduced.

Sixth Embodiment

A sixth embodiment of the present disclosure will next be described.

A biological information measuring apparatus according to the present embodiment has the same configuration as that of the biological information measuring apparatus 1G according to the fifth embodiment but differs therefrom in that a concave curved surface connected to the outer edge of the second convex curved surface is formed in the recess. In the following description, the same or substantially the same portion having been already described has the same reference character and will not be described.

Figure 14:
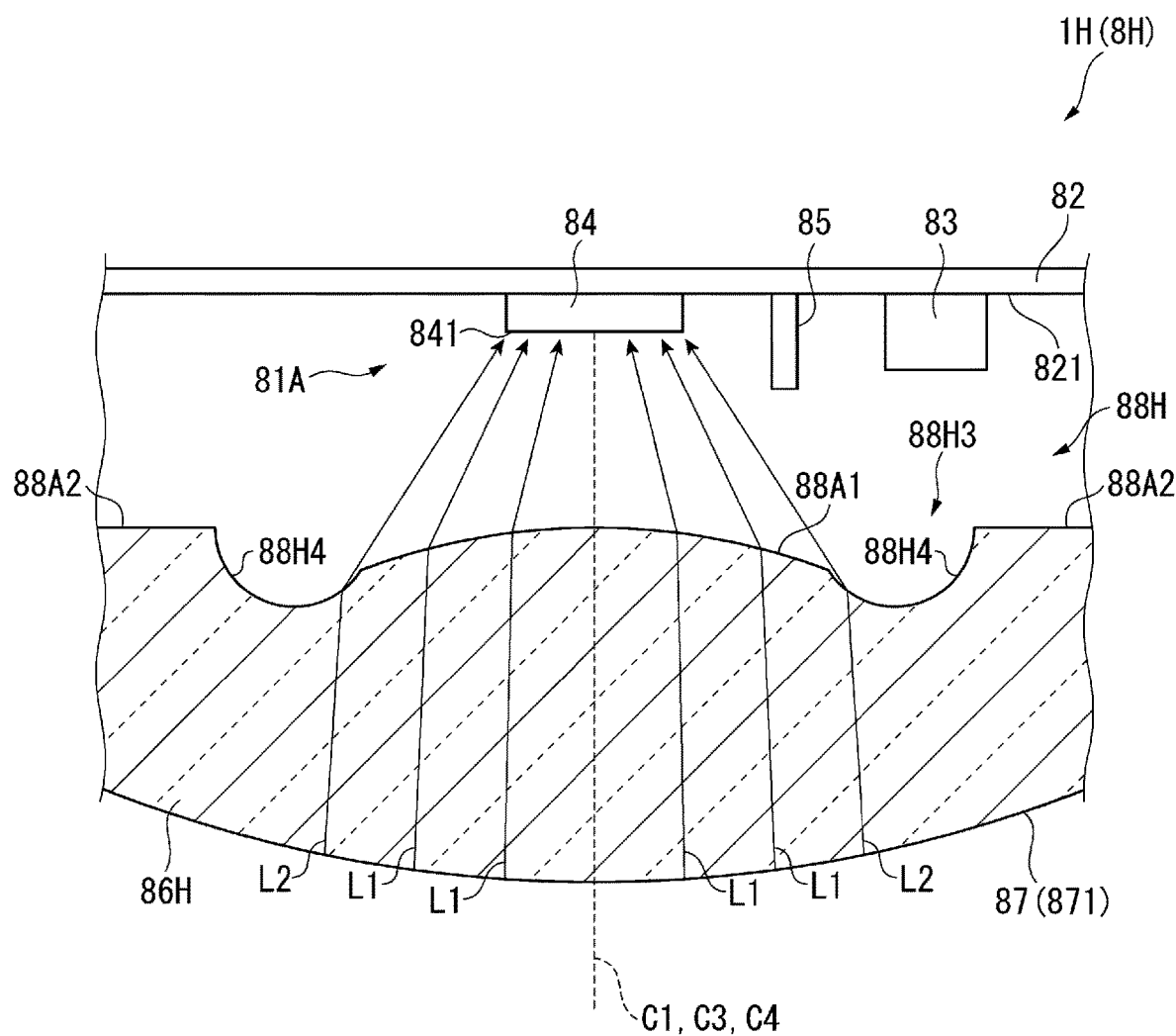
FIG. 14 is a cross-sectional view showing a biological sensor module provided in a biological information measuring apparatus according to a sixth embodiment of the present disclosure.

FIG. 14 is a cross-sectional view showing a biological sensor module 8H provided in a biological information measuring apparatus 1H according to the present embodiment. In detail, FIG. 14 shows the cross section of the biological sensor module 8H taken along the plane XZ.

The biological information measuring apparatus 1H according to the present embodiment has the same configuration and function as those of the biological information measuring apparatus 1G except that the biological sensor module 8G is replaced with the biological sensor module 8H. The biological sensor module 8H has the same configuration as that of the biological sensor module 8G except that the passage section 86G is replaced with a passage section 86H. That is, the biological sensor module 8H includes the sensor section 81A and the passage section 86H.

The passage section 86H is a light transmissive member that is fit into the opening 222, protects the sensor section 81A, and transmits the first light emitted from the light emitter 83 and the second light to be received by the light receiver 84.

The passage section 86H includes the outer surface section 87, which has the first convex curved surface 871, and an inner surface section 88H, which is opposite the outer surface section 87 and faces the light emitter 83 and the light receiver 84.

The center C1 of the first convex curved surface 871 coincides with the center of the contact section 221 and the center C3 of the light receiver 84 in the plan view.

The inner surface section 88H includes a recess 88H3, in which the second convex curved surface 88A1 is located, and the flat surface 88A2, which is located in the area outside the recess 88H3.

The center C4 of the second convex curved surface 88A1 having a circular shape in the plan view coincides with the centers C1 and C3 in the present embodiment, but not necessarily. The center C4 is so set as to fall within the range including the center C1 of the first convex curved surface 871 and the center C3 of the light receiver 84 and between the center C1 and the center C3.

The range over which the second convex curved surface 88A1 is formed in the plan view is so set as to contain an area that overlaps with at least part of the light receiver 84 having an oblong shape and the area that does not overlap with the light receiver 84.

An arcuate concave curved surface 88H4, which is continuous with the outer edge of the second convex curved surface 88A1, is formed in the recess 88H3 in the plan view. Specifically, the concave curved surface 88H4 is so formed in a substantially semicircular shape in a cross-sectional view as to be recessed toward the positive side in the direction Z.

The concave curved surface 88H4 acts as a concave lens that diffuses the second light passing through the passage section 86H from the positive side in the direction Z. Therefore, not only second light L1, which is incident on the first convex curved surface 871 and passing through the second convex curved surface 88A1, but second light L2, which is incident from the positive side in the direction Z, for example, on an area of the concave curved surface 88H4 that is the area close to the second convex curved surface 88A1 and refracted at the concave curved surface 88H4, travel toward the light receiver 84. A greater amount of second light can thus be collected into a spot on the light receiver 84.

Effects Provided by Sixth Embodiment

The biological information measuring apparatus 1H according to the present embodiment described above can provide the same effects as those provided by the biological information measuring apparatus 1G and can further provide the following effect.

The inner surface section 88H, which forms the passage section 86H, has the concave curved surface 88H4, which is continuous with the outer edge of the second convex curved surface 88A1, in the recess 88H3. Therefore, since the concave curved surface 88H4 functions as a concave lens that diffuses the second light incident from the positive side in the direction Z, the second light incident on part of the concave curved surface 88H4 is allowed to be incident on the light receiver 84. The amount of second light received by the light receiver 84 can therefore be increased, whereby the pulse wave can be detected with higher precision.

Seventh Embodiment

A seventh embodiment of the present disclosure will next be described.

A biological information measuring apparatus according to the present embodiment has the same configuration as that of the biological information measuring apparatus 1A shown in the first embodiment but differs therefrom in that a biological sensor module in which the sensor section and the passage section are integrated with each other is provided. In the following description, the same or substantially the same portion having been already described has the same reference character and will not be described.

Figure 15:
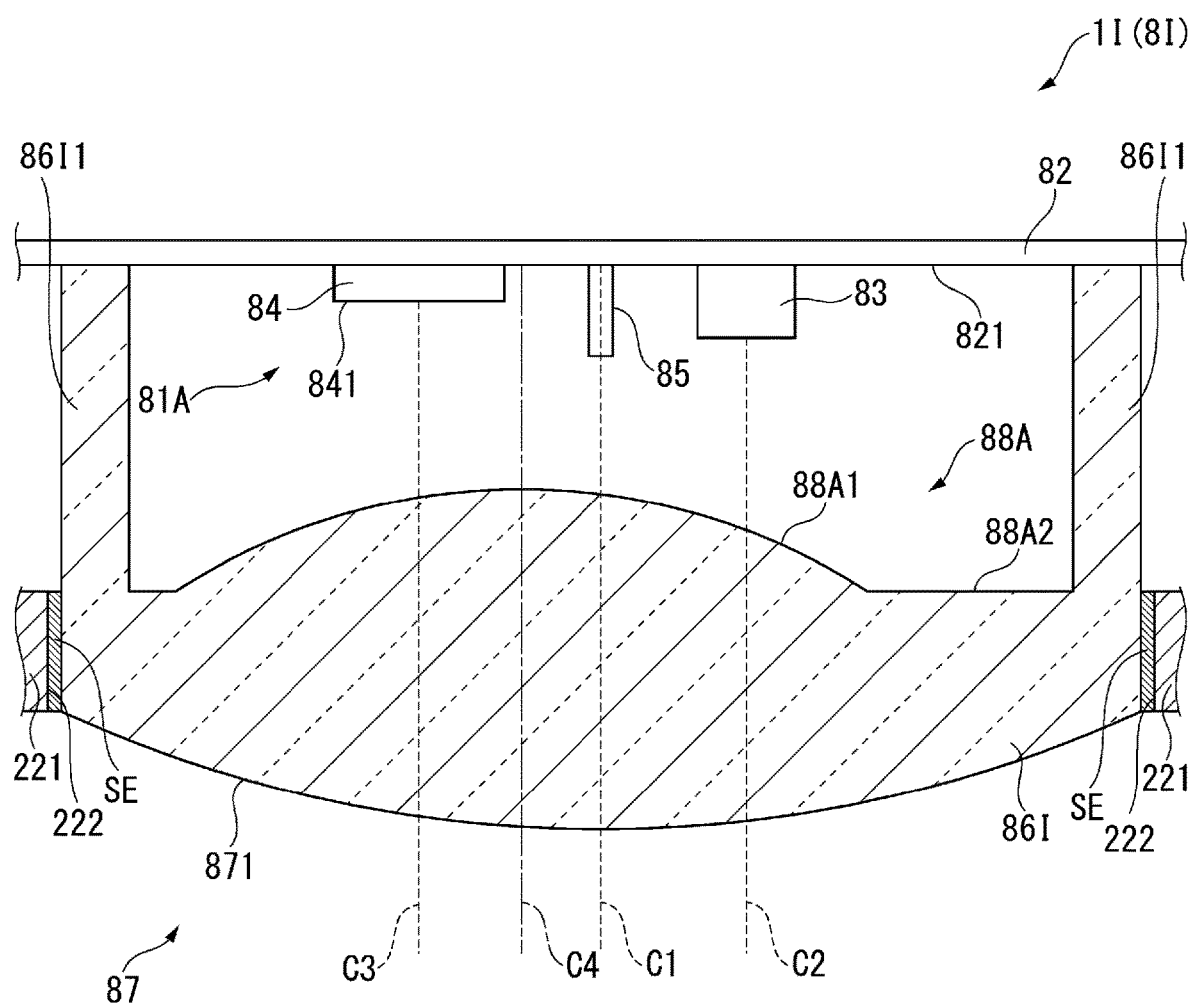
FIG. 15 is a cross-sectional view showing a biological sensor module provided in a biological information measuring apparatus according to a seventh embodiment of the present disclosure.

FIG. 15 is a cross-sectional view showing a biological sensor module 8I provided in a biological information measuring apparatus 1I according to the present embodiment. In detail, FIG. 15 shows the cross section of the biological sensor module 8I taken along a plane parallel to the plane XZ.

The biological information measuring apparatus 1I according to the present embodiment has the same configuration and function as those of the biological information measuring apparatus 1A except that the biological sensor module 8A is replaced with the biological sensor module 8I.

The biological sensor module 8I detects biological information from the user's body, which is a living body, as the biological sensor module 8A does. The biological sensor module 8I includes the sensor section 81A and a passage section 86I, as shown in FIG. 15.

The passage section 86I includes the outer surface section 87, which has the first convex curved surface 871, and the inner surface section 88A, which includes the second convex curved surface 88A1 and the flat surface 88A2, as the passage section 86A does, and further includes a fixed section 86I1.

The fixed section 86I1 extends from a portion of the inner surface section 88A that is the portion outside the second convex curved surface 88A1 toward the substrate 82 of the sensor section 81A and is fixed to the +Z-direction-side surface 821 of the substrate 82. In detail, the fixed section 86I1 extends from an outer edge portion of the passage section 86I, which is formed in a substantially circular shape in accordance with the opening 222 when viewed from the positive side in the direction Z, toward the substrate 82. The passage section 86I and the substrate 82 and in turn the sensor section 81A are therefore integrated with one another. Any of the passage sections 86A to 86H described above may be provided with the thus configured fixed section 86I1.

In the thus configured biological sensor module 8I, the passage section 86I is disposed in the opening 222, as the passage sections 86A to 86H described above are. However, since the passage section 86I is fixed to the substrate 82 via the fixed section 86I1, a gap could be created between the inner edge of the opening 222 and the outer edge of the passage section 86I due, for example, to dimensional tolerance. Such a gap could degrade waterproofness and dustproofness of the biological information measuring apparatus 1I.

To avoid the problem, in the present embodiment, a sealing member SE, which fills the gap between the inner edge of the opening 222 and the outer edge of the passage section 86I, is provided. The sealing member SE is made, for example, of a sealing material filled in the gap between the inner edge of the opening 222 and the outer edge of the passage section 86I. The sealing member SE can ensure the waterproofness and dustproofness of the biological information measuring apparatus 1I even in the case where the biological sensor module 8I is provided in the opening 222.

The biological information measuring apparatus 1I according to the present embodiment described above can provide the same effects as those provided by the biological information measuring apparatus 1A.

Variations of Embodiment

The present disclosure is not limited to the embodiments described above, and changes, improvements, and other modifications to the extent that the advantage of the present disclosure is achieved fall within the scope of the present disclosure.

The configurations of the biological sensor modules 8A to 8I shown in the embodiments described above may be combined with one another. For example, the inner surface sections 88A to 88E of the biological sensor modules 8A to 8E may each be provided with the recess 88G3 or 88H3 of the inner surface section 88G or 88H or may be provided with the concave curved surface 88H4 of the inner surface section 88H.

The passage sections 86A to 86H, which form the biological sensor modules 8A to 8H, may include a fixed section similar to the fixed section 86I1, as described above, or the substrate 82 may include a fixing section that fixes the passage section. Further, the light emitter, the light receiver, and the passage section may not be integrated with one another by the substrate on which the light emitter and the light receiver are disposed and may instead be integrated with one another in another configuration.

In addition, the number of light emitters and the number of light receivers provided in the sensor section can be changed as appropriate, and the layout of the light emitter and the light receiver can be changed as appropriate, as described above. For example, in a case where at least one of the light emitter and the light receiver is formed of a plurality of light emitters or light receives, the light emitters and the light receivers are not necessarily so disposed that the centers thereof are located on an imaginary straight line along the direction +X and may instead be so disposed that the centers thereof are located on an imaginary straight line along the direction +Y.

In the embodiments described above, the centers of the second convex curved surfaces 88A1, 88B1, 88C1, 88D1, 88E1, and 88F1 are so set as to fall within the range including the center of the first convex curved surface and the center of the light receiver and between the center of the first convex curved surface and the center of the light receiver in the plan view, but not necessarily. The center of the second convex curved surface can be changed as appropriate in consideration, for example, of the range over which the second convex curved surface is formed in the plan view. The range over which the second convex curved surface is formed in the plan view can also be changed as appropriate. For example, the range contains not only the light receiver 84 as described above but the light emitter 83.

In the embodiments described above, the measurement section 4 includes the acceleration sensor 41, which detects acceleration acting on the biological information measuring apparatus, in addition to the biological sensor module, but not necessarily. The acceleration sensor 41 may not be provided. The biological information measuring apparatus may include another sensor, such as a position sensor capable of measuring position information (GPS receiver, for example).

In the embodiments described above, the biological sensor modules 8A to 8H detect the pulse wave, which is one piece of biological information, and the processing section determines the pulse rate, which is another piece of biological information, based on the detection signal outputted from the biological sensor modules 8A to 8H. That is, the biological information measuring apparatuses 1A to 1H described above measure the pulse wave and the pulse rate as the biological information, but not necessarily. The biological information that the biological sensor module and the biological information measuring apparatus according to any of the embodiments of the present disclosure can detect and measure is not limited to the pulse wave or the pulse rate. For example, the present disclosure may be applied to a biological information measuring apparatus that measures other pieces of biological information, such as the heart rate variability (RV), R-R interval (RRI: interval between pulses), blood pressure, blood sugar level, the amount of activity, consumed calorie, and maximum oxygen uptake ($VO_2$max).

In the embodiments described above, the biological sensor module according to any of the embodiments of the present disclosure is used in the biological information measuring apparatus worn on the user's wrist by way of example, but not necessarily. The portion where the biological information measuring apparatus is worn may instead be the user's ankle or any other portion. An electronic instrument in which the biological sensor module is incorporated is not limited to a biological information measuring apparatus dedicated to measurement of biological information.

What is claimed is:

1. A biological sensor module comprising:
   a substrate;
   a light emitter that emits irradiation light to a living body, the light emitter being disposed on a first surface of the substrate that faces the living body;
   a light receiver that receives reflected light that is the irradiation light reflected off the living body, the light receiver being disposed on the first surface of the substrate; and
   a passage section including an outer surface section having a first convex curved surface configured to press the living body and an inner surface section that is opposite the outer surface section and has a second convex curved surface that collects the reflected light into a spot on the light receiver, wherein
   a radius of curvature of the second convex curved surface is smaller than a radius of curvature of the first convex curved surface in a cross section parallel to a plane specified by a first direction that is a direction from the light emitter toward the light receiver and a second direction that is a direction from the inner surface section toward the outer surface section,
   the first direction is perpendicular to the second direction,
   the first surface of the substrate faces the first convex curved surface and the second convex curved surface, and
   wherein a center of the second convex curved surface is so set as to fall within a range including a center of the light receiver and a center of the first convex curved surface.

2. The biological sensor module according to claim 1, wherein the inner surface section includes a recess that is recessed in the second direction, and
   the second convex curved surface is located in the recess.

3. The biological sensor module according to claim 2, wherein the inner surface section is located in the recess and has a concave curved surface continuous with an outer edge of the second convex curved surface.

4. The biological sensor module according to claim 1, wherein the second convex curved surface has a portion that does not overlap with the light receiver when viewed along the second direction.

5. The biological sensor module according to claim 4, wherein the inner surface section includes a recess that is recessed in the second direction, and
   the second convex curved surface is located in the recess.

6. The biological sensor module according to claim 5, wherein the inner surface section is located in the recess and has a concave curved surface continuous with an outer edge of the second convex curved surface.

7. The biological sensor module according to claim 1, wherein the center of the second convex curved surface is so set as to fall between the center of the light receiver and the center of the first convex curved surface when viewed along the second direction.

8. The biological sensor module according to claim 7, wherein the second convex curved surface has a portion that does not overlap with the light receiver when viewed along the second direction.

9. The biological sensor module according to claim 7, wherein the inner surface section includes a recess that is recessed in the second direction, and
   the second convex curved surface is located in the recess.

10. The biological sensor module according to claim 9, wherein the inner surface section is located in the recess and has a concave curved surface continuous with an outer edge of the second convex curved surface.

11. A biological information measuring apparatus comprising:
    a biological sensor module including
      a substrate;
      a light emitter that emits irradiation light to a living body, the light emitter being disposed on a first surface of the substrate that faces the living body,
      a light receiver that receives reflected light that is the irradiation light reflected off the living body, the light receiver being disposed on the first surface of the substrate, and
      a passage section including an outer surface section having a first convex curved surface configured to press the living body and an inner surface section that is opposite the outer surface section and has a second convex curved surface that collects the reflected light into a spot on the light receiver;
    a housing in which the biological sensor module is provided; and
    a processing circuit that calculates biological information based on a signal outputted from the light receiver, wherein
    a radius of curvature of the second convex curved surface is smaller than a radius of curvature of the first convex curved surface in a cross section parallel to a plane specified by a first direction that is a direction from the light emitter toward the light receiver and a second direction that is a direction from the inner surface section toward the outer surface section,
    the first direction is perpendicular to the second direction,
    the first surface of the substrate faces the first convex curved surface and the second convex curved surface and wherein a center of the second convex curved surface is so set as to fall within a range including a center of the light receiver and a center of the first convex curved surface.

12. The biological information measuring apparatus according to claim 11,
wherein the housing includes a contact section that has an opening in which the passage section is disposed and configured to come into contact with the living body, and
wherein the center of the first convex curved surface coincides with a center of the contact section when viewed along the second direction.

13. The biological information measuring apparatus according to claim 11,
wherein the center of the second convex curved surface is so set as to fall between the center of the light receiver and the center of the first convex curved surface when viewed along the second direction.

* * * * *